United States Patent
Klosin et al.

(10) Patent No.: US 9,522,855 B2
(45) Date of Patent: Dec. 20, 2016

(54) PROCESS FOR PRODUCING LOW MOLECULAR WEIGHT ETHYLENE- AND ALPHA-OLEFIN-BASED MATERIALS

(71) Applicant: DOW GLOBAL TECHNOLOGIES LLC, Midland, MI (US)

(72) Inventors: Jerzy Klosin, Midland, MI (US); Pulikkottil J. Thomas, Midland, MI (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 190 days.

(21) Appl. No.: 14/361,552

(22) PCT Filed: Nov. 28, 2012

(86) PCT No.: PCT/US2012/066698
§ 371 (c)(1),
(2) Date: May 29, 2014

(87) PCT Pub. No.: WO2013/101375
PCT Pub. Date: Jul. 4, 2013

(65) Prior Publication Data
US 2014/0357918 A1    Dec. 4, 2014

Related U.S. Application Data

(60) Provisional application No. 61/581,465, filed on Dec. 29, 2011.

(51) Int. Cl.
| | | |
|---|---|---|
| *C08F 4/06* | (2006.01) | |
| *C08F 4/18* | (2006.01) | |
| *C08F 210/00* | (2006.01) | |
| *C07C 2/26* | (2006.01) | |
| *C07C 2/32* | (2006.01) | |
| *C08F 10/00* | (2006.01) | |

(52) U.S. Cl.
CPC ............... *C07C 2/32* (2013.01); *C08F 10/00* (2013.01); *C07C 2531/22* (2013.01)

(58) Field of Classification Search
CPC ... C08F 10/00; C08F 4/64186; C08F 4/64189; C08F 4/64193; C08F 4/64196; C07C 2/32; C07C 253/22
USPC .......................... 585/511; 526/107, 100, 348
See application file for complete search history.

(56) References Cited

U.S. PATENT DOCUMENTS

| | | |
|---|---|---|
| 5,064,802 A | 11/1991 | Stevens et al. |
| 5,153,157 A | 10/1992 | Hlatky et al. |
| 5,296,433 A | 3/1994 | Siedle et al. |
| 5,321,106 A | 6/1994 | LaPointe |
| 5,350,723 A | 9/1994 | Neithamer et al. |
| 5,425,872 A | 6/1995 | Devore et al. |
| 5,625,087 A | 4/1997 | Devore et al. |
| 5,721,185 A | 2/1998 | LaPointe et al. |
| 5,783,512 A | 7/1998 | Jacobsen et al. |
| 5,883,204 A | 3/1999 | Spencer et al. |
| 5,919,983 A | 7/1999 | Rosen et al. |
| 6,696,379 B1 | 2/2004 | Carnahan et al. |
| 6,869,904 B2 | 3/2005 | Boussie et al. |
| 6,924,342 B2 | 8/2005 | Stevens et al. |
| 7,060,848 B2 | 6/2006 | Boussie et al. |
| 7,163,907 B1 | 1/2007 | Canich et al. |
| 8,609,794 B2 * | 12/2013 | Klosin ............... C08F 10/00 502/103 |
| 9,000,108 B2 * | 4/2015 | Klosin ............... C08F 10/00 526/161 |
| 2011/0002820 A1 | 1/2011 | Klosin et al. |
| 2014/0163186 A1 | 6/2014 | Klosin et al. |

FOREIGN PATENT DOCUMENTS

| | | |
|---|---|---|
| WO | 2005/108406 A1 | 11/2005 |
| WO | 2007136497 A2 | 11/2007 |
| WO | WO 2007/136495 A2 * | 11/2007 |
| WO | 2011/146044 A1 | 11/2011 |
| WO | 2013/101375 A1 | 7/2013 |

OTHER PUBLICATIONS

PCT/US2012/066698, International Search Report, mailed Feb. 5, 2013.
PCT/US2012/066698, International Preliminary Report on Patentability, mailed Jul. 20, 2014.

* cited by examiner

Primary Examiner — William Cheung
(74) Attorney, Agent, or Firm — Husch Blackwell LLP

(57) ABSTRACT

The present invention generally relates to a process that prepares polyethylenes, poly-α-olefins or poly(co-ethylene-α-olefin) having backbone weight average molecular weights less than 2500 daltons. The process uses a metal-ligand complex as a precatalyst and can be carried out at temperatures ranging from 30° C. to 300° C. The relatively low molecular weight of the products enables improved viscosity control for a wide variety of applications.

9 Claims, No Drawings

PROCESS FOR PRODUCING LOW MOLECULAR WEIGHT ETHYLENE- AND ALPHA-OLEFIN-BASED MATERIALS

This application is a U.S. National Stage Application under 35 U.S.C. §371 of International Application No. PCT/US2012/066698 filed on Nov. 28, 2012, which claims priority from the U.S. Provisional Patent Application No. 61/581,465, on Dec. 29, 2011, entitled "Process For Producing Low Molecular Weight Ethylene- and Alpha-Olefin-Based Materials," the teachings of which are incorporated by reference herein as if reproduced in full herein below.

The present invention relates to a process for preparing low molecular weight polyethylene, poly-α-olefins and poly (co-ethylene-α-olefins) at a wide range of reactor temperatures.

Low molecular weight ethylene-based polymers are highly desirable due to their potential use in many applications such as, for example, synthetic oils in automotive applications, transformer fluids in electrical applications, lubricants, adhesives and high temperature fluids. Most processes that produce such a low molecular ethylene-based materials are produced at temperatures below 100° C. From the process prospective, it might be desirable to produce such ethylene-based materials at higher reactor temperature. Such temperatures are defined as above about 100 degrees Celsius (° C.), and generally up to about 250° C.

In view of this, researchers have sought ways to produce low molecular weight ethylene-based products while still enjoying the benefits of high temperature processing, such as rapid polymerization. Various forays into the catalyst art have, in general, resulted in products of various molecular weights, but none has to date resulted in high temperature application to produce very low molecular weight polymers.

In view of this, researchers have sought ways to produce low molecular weight ethylene-based products while still enjoying the benefits of high temperature processing, such as rapid polymerization. Various forays into the catalyst art have, in general, resulted in products of various molecular weights, but none has to date resulted in high temperature application to produce very low molecular weight polymers. Among these forays are, for example, U.S. Pat. Nos. 6,869,904 and 7,060,848. These patents disclose ligands, and metal-ligand complexes with substituted bridged bis-aromatic or bridged bis-bi-aromatic ligands. As catalysts, these complexes offer high comonomer incorporation into ethylene/α-olefin copolymers, where such olefins are, for example, 1-octene, propylene or styrene.

In one aspect, the present invention is a process for preparing a low molecular weight ethylene-based material comprising a step of contacting together (1) a monomer selected from (a) ethylene; (b) a non-ethylene α-olefin; or (c) a combination thereof; and (2) a catalytic amount of a catalyst; wherein the catalyst comprises a mixture or reaction product of ingredients (2a) and (2b) that is prepared before the contacting step, wherein ingredient (2a) is at least one metal-ligand complex, and wherein ingredient (2b) is at least one activating co-catalyst; the metal-ligand complex of ingredient (2a) being at least one metal-ligand complex of formula (I):

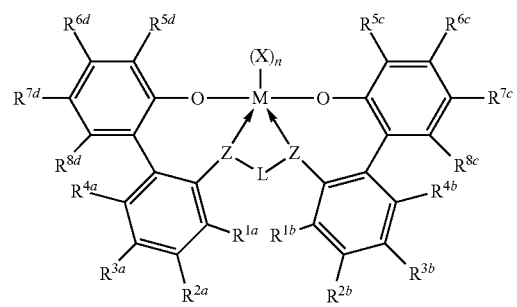

wherein M is titanium, zirconium, or hafnium, each independently being in a formal oxidation state of +2, +3, or +4; n is an integer from 0 to 3, wherein when n is 0, X is absent; each X independently is a monodentate ligand that is neutral, monoanionic, or dianionic, or two X are taken together to form a bidentate ligand that is neutral, monoanionic, or dianionic; X and n are chosen in such a way that the metal-ligand complex of formula (I) is, overall, neutral; each Z independently is O, S, N($C_1$-$C_{40}$)hydrocarbyl, or P($C_1$-$C_{40}$)hydrocarbyl; L is ($C_1$-$C_{40}$)hydrocarbylene or ($C_1$-$C_{40}$) heterohydrocarbylene, wherein the ($C_1$-$C_{40}$)hydrocarbylene has a portion that comprises a 2-carbon atom linker backbone linking the Z atoms in formula (I) and the ($C_1$-$C_{40}$) heterohydrocarbylene has a portion that comprises a 2-atom atom linker backbone linking the Z atoms in formula (I), wherein each atom of the 2-atom linker of the ($C_1$-$C_{40}$) heterohydrocarbylene independently is a carbon atom or a heteroatom, wherein each heteroatom independently is O, S, S(O), S(O)$_2$, Si($R^C$)$_2$, Ge($R^C$)$_2$, P($R^P$), or N($R^N$), wherein independently each $R^C$ is unsubstituted ($C_1$-$C_{18}$)hydrocarbyl or the two $R^C$ are taken together to form a ($C_2$-$C_{19}$)alkylene, each $R^P$ is unsubstituted ($C_1$-$C_{18}$)hydrocarbyl; and each $R^N$ is unsubstituted ($C_1$-$C_{18}$)hydrocarbyl, a hydrogen atom or absent; at least one of $R^{1a}$, $R^{2a}$, $R^{1b}$, and $R^{2b}$ independently is a ($C_1$-$C_{40}$)hydrocarbyl, ($C_1$-$C_{40}$)heterohydrocarbyl, N($R^N$)$_2$, NO$_2$, O$R^C$, S$R^C$, Si($R^C$)$_3$, Ge($R^C$)$_3$, CN, CF$_3$, F$_3$CO, halogen atom, and each of the others of $R^{1a}$, $R^{2a}$, $R^{1b}$, and $R^{2b}$ independently is a hydrogen, ($C_1$-$C_{40}$)hydrocarbyl, ($C_1$-$C_{40}$)heterohydrocarbyl, N($R^N$)$_2$, NO$_2$, O$R^C$, S$R^C$, Si($R^C$)$_3$, CN, CF$_3$, F$_3$CO or halogen atom; each of $R^{3a}$, $R^{4a}$, $R^{3b}$, $R^{4b}$, $R^{6c}$, $R^{7c}$, $R^{8c}$, $R^{6d}$, $R^{7d}$, and $R^{8d}$ independently is a hydrogen atom; ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, O$R^C$, S$R^C$, NO$_2$, CN, CF$_3$, $R^C$S(O)—, $R^C$S(O)$_2$—, ($R^C$)$_2$C=N—, $R^C$C (O)O—, $R^C$OC(O)—, $R^C$C(O)N(R)—, ($R^C$)$_2$NC(O)— or halogen atom; each of $R^{5c}$ and $R^{5d}$ independently is a ($C_6$-$C_{40}$)aryl or ($C_1$-$C_{40}$)heteroaryl; each of the aforementioned aryl, heteroaryl, hydrocarbyl, heterohydrocarbyl, hydrocarbylene, and heterohydrocarbylene groups independently is unsubstituted or substituted with one or more substituents $R^S$; and each $R^S$ independently is a halogen atom, polyfluoro substitution, perfluoro substitution, unsubstituted ($C_1$-$C_{18}$)alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the $R^S$ are taken together to form an unsubstituted ($C_1$-$C_{18}$)alkylene, wherein each R independently is an unsubstituted ($C_1$-$C_{18}$)alkyl; such that the ratio of total number of moles of the at least one metal-ligand complex of (2a) to total number of moles of the at least one activating co-catalyst of (2b) is from 1:10,000 to 100:1; under conditions such that a polyethylene, poly-α-olefin, or, poly(co-ethylene-α-olefin), having a backbone weight average molecular weight (Mw) that is less than 2500 daltons (Da), is formed.

The invention offers a process to prepare low molecular weight polymers based on ethylene, an α-olefin, or both, using as a catalyst one or more of a group of compounds having in common (1) a two-atom bridge between bis-ether oxygen atoms, and (2) a substituent group positioned ortho and/or meta to the di-ether bridge. These two features, in particular, have been found to afford these catalysts with a unique capability to produce surprisingly low molecular weight polyethylene, poly(co-ethylene-α-olefins) and poly-α-olefins, generally having backbone weight average molecular weights less than 2500 Da, preferably less than 1500 Da, even when processing is accomplished over a wide range of temperatures ranging from 30° C. to 300° C. Because of their surprisingly low molecular weights, these products exhibit controlled viscosity and are generally liquids, increasing the number of potential applications for them. The term "low molecular weights" refers to materials which may include dimers, trimers, tetramers, etc., up to backbone weight average molecular weights of less than 2500 Da.

Preparation of the low molecular weight polyethylene, poly(α-olefin) or poly(co-ethylene-α-olefin) herein is generally by contact between the selected catalyst or catalysts and the other starting ingredients, with a first step comprising contacting the metal-ligand complex with a suitable activating co-catalyst to form a catalyst, followed by contact between the catalyst, or catalysts, and either the ethylene or the selected combination of ethylene and at least one α-olefin, under suitable reaction conditions to form the final desired product.

In general the catalysts useful in the present invention fall within the group defined by co-pending U.S. Patent Publication No. 2011/0282018, filed May 11, 2011. However, the catalysts used herein form a subset thereof that exhibits surprising capabilities not shared by other members of that group, notably to make a polyethylene, a poly(α-olefin) or a poly(co-ethylene-α-olefin) that has a surprisingly low molecular weight.

In some embodiments, each of the chemical groups (e.g., X, L, $R^{1a}$, etc.) of the metal-ligand complex of formula (I) is unsubstituted, that is, can be defined without use of a substituent $R^S$. In other embodiments, at least one of the chemical groups of the metal-ligand complex independently contains one or more of the substituents $R^S$. Preferably, there are not more than a total of 20 $R^S$, more preferably not more than 10 $R^S$, and still more preferably not more than 5 $R^S$. Where the invention compound contains two or more substituents $R^S$, each $R^S$ independently is bonded to a same or different substituted chemical group. When two or more $R^S$ are bonded to a same chemical group, they independently are bonded to a same or different carbon atom or heteroatom in the same chemical group, up to and including persubstitution of the chemical group.

The terms "persubstitution" means each hydrogen atom (H) bonded to a carbon atom or heteroatom of a corresponding unsubstituted compound or functional group is replaced by a substituent (e.g., $R^S$). The term, "polysubstitution" means at least two, but not all, hydrogen atoms (H) bonded to carbon atoms or heteroatoms of a corresponding unsubstituted compound or functional group are replaced by substituents (e.g., $R^S$). In some embodiments, at least one $R^S$ is polyfluoro substitution or perfluoro substitution.

As used herein, "polyfluoro substitution" and "perfluoro substitution" each count as one $R^S$ substituent. In some embodiments each $R^S$ independently is selected from a group consisting of a halogen atom and any one of polyfluoro substitution, unsubstituted $(C_1-C_{18})$alkyl, $F_3C$—, $FCH_2O$—, $F_2HCO$—, $F_3CO$—, $R_3Si$—, $R_3Ge$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—, wherein each R independently is an unsubstituted $(C_1-C_{18})$alkyl. In some embodiments each $R^S$ independently is selected from a group consisting of a halogen atom, unsubstituted $(C_1-C_{18})$alkyl, and any one of polyfluoro substitution, $F_3C$—, $FCH_2O$—, $F_2HCO$—, $F_3CO$—, $R_3Si$—, $R_3Ge$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—. In some embodiments each $R^S$ independently is selected from a group consisting of an unsubstituted $(C_1-C_{18})$alkyl and any one of $F_3C$—, $FCH_2O$—, $F_2HCO$—, $F_3CO$—, $R_3Si$—, $R_3Ge$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, and $R_2NC(O)$—. In some embodiments two $R^S$ are taken together to form an unsubstituted $(C_1-C_{18})$alkylene. Still more preferably substitutents $R^S$ independently are unsubstituted $(C_1-C_{18})$alkyl, F, unsubstituted $(C_1-C_{18})$alkylene, or a combination thereof; and even more preferably unsubstituted $(C_1-C_8)$alkyl or unsubstituted $(C_1-C_8)$alkylene. The $(C_1-C_{18})$alkylene and $(C_1-C_8)$alkylene substituents are especially useful for forming substituted chemical groups that are bicyclic or tricyclic analogs of corresponding monocyclic or bicyclic unsubstituted chemical groups.

The term "hydrocarbylene" means a hydrocarbon diradical having at least one carbon atom, such that each hydrocarbon diradical independently is aromatic or non-aromatic; saturated or unsaturated; straight chain or branched chain; cyclic or acyclic; unsubstituted or substituted; or a combination of at least two thereof. The radicals of the hydrocarbon diradical can be on a single carbon atom or, preferably, different carbon atoms. The term "alkylene" is a hydrocarbylene wherein the hydrocarbon diradical is non-aromatic, saturated, straight chain or branched, acyclic, and unsubstituted or substituted. The term "hydrocarbyl" is as defined previously for hydrocarbylene, except where hydrocarbylene is the diradical, the hydrocarbyl is a monoradical and thus has a hydrogen atom in place of the second radical of the diradical. The term "alkyl" is a hydrocarbyl wherein the hydrocarbon radical is non-aromatic, saturated, straight chain or branched, acyclic, and unsubstituted or substituted. Preferably, the substituent of the substituted alkyl is aryl. The term "heterohydrocarbylene" means a heterohydrocarbon diradical having at least one carbon atom and from 1 to 6 heteroatoms, wherein each heterohydrocarbon diradical independently is aromatic or non-aromatic; saturated or unsaturated; straight chain or branched chain; cyclic or acyclic; unsubstituted or substituted; or a combination of at least two thereof. The radicals of the heterohydrocarbon diradical can be on a single atom or, preferably, different atoms, each radical-bearing atom independently being carbon or heteroatom. The term "heterohydrocarbyl" is as defined previously for heterohydrocarbylene, except where heterohydrocarbylene is the diradical, the heterohydrocarbyl is a monoradical.

In some embodiments the present invention contemplates such unsubstituted chemical groups or molecules having a lower limit of at least 1 carbon atom. However, the invention includes embodiments having higher lower limits (e.g., at least any one of 2, 3, 4, 5, 6, 7, and 8 carbons). In particular, embodiments including higher lower limits as would be well known for a smallest aspect of the chemical group or molecule (e.g., at least 3 carbons for a cycloalkyl or α-olefin) may be particularly preferred.

Preferably, each hydrocarbyl independently is an unsubstituted or substituted alkyl, cycloalkyl (having at least 3 carbon atoms), $(C_3-C_{20})$cycloalkyl-$(C_1-C_{20})$alkylene, aryl (having at least 6 carbon atoms), or $(C_6-C_{20})$aryl-$(C_1-C_{20})$alkylene. Preferably, each of the aforementioned hydrocarbyl groups independently has a maximum of 40, more preferably 20, and still more preferably 12 carbon atoms.

Preferably, each alkyl independently has a maximum of 40, more preferably 20, sill more preferably 12, and still more preferably 8 carbon atoms. A few non-limiting examples of unsubstituted $(C_1-C_{40})$alkyl include unsubstituted $(C_1-C_{20})$alkyl; unsubstituted $(C_1-C_{10})$alkyl; unsubstituted $(C_1-C_5)$alkyl; methyl; ethyl; 1-propyl; 2-methylpropyl; 1,1-dimethylethyl; and 1-heptyl. Non-limiting examples of substituted $(C_1-C_{40})$alkyl include substituted $(C_1-C_{20})$alkyl, substituted $(C_1-C_{10})$alkyl, trifluoromethyl, and $(C_{45})$alkyl. The $(C_{45})$alkyl may be, for example, a $(C_{27}-C_{40})$alkyl substituted by one $R^S$, which is a $(C_{18}-C_5)$alkyl, respectively. Preferably, each $(C_1-C_5)$alkyl independently is methyl, trifluoromethyl, ethyl, 1-propyl, 2-methylethyl, or 1,1-dimethylethyl.

Preferably, each aryl independently has from 6 to 40 carbon atoms. The term "$(C_6-C_{40})$aryl" means an unsubstituted or substituted (by at least one $R^S$) mono-, bi- or tricyclic aromatic hydrocarbon radical of from 6 to 40, preferably from 6 to 14, ring carbon atoms, and the mono-, bi- or tricyclic radical comprises 1, 2 or 3 rings, respectively, wherein the 1 ring is aromatic; at least one of the 2 or 3 rings is aromatic; and the 2 or 3 rings independently are fused or non-fused. Other aryl groups (e.g., $(C_6-C_{10})$aryl)) are defined in an analogous manner. Preferably, $(C_6-C_{40})$aryl has a maximum of 20 carbon atoms (i.e., $(C_6-C_{20})$aryl), more preferably 10 carbon atoms, and still more preferably 6 carbon atoms. Non-limiting examples of unsubstituted $(C_6-C_{40})$aryl include unsubstituted $(C_6-C_{20})$aryl; unsubstituted $(C_6-C_{18})$aryl; phenyl; $(C_3-C_6)$cycloalkyl-phenyl; fluorenyl; tetrahydrofluorenyl; indacenyl; hexahydroindacenyl; indenyl; dihydroindenyl; naphthyl; tetrahydronaphthyl; and phenanthrene. Examples of substituted $(C_6-C_{40})$aryl are substituted $(C_6-C_{20})$aryl; substituted $(C_6-C_{18})$aryl; 2-$(C_1-C_5)$alkyl-phenyl; 2,4-bis$(C_1-C_5)$alkyl-phenyl; 2,4-bis[$(C_{20})$alkyl]-phenyl; polyfluorophenyl; pentafluorophenyl; and fluoren-9-one-1-yl.

Preferably, each cycloalkyl independently has from 3 to 40 carbon atoms. The term "$(C_3-C_{40})$cycloalkyl" means a saturated cyclic hydrocarbon radical of from 3 to 40 carbon atoms that is unsubstituted or substituted by at least one $R^S$. Other cycloalkyl groups (e.g., $(C_3-C_{12})$alkyl)) are defined in an analogous manner. Preferably, $(C_3-C_{40})$cycloalkyl has a maximum of 20 carbon atoms (i.e., $(C_3-C_{30})$cycloalkyl), and more preferably 6 carbon atoms. Non-limiting examples of unsubstituted $(C_3-C_{40})$cycloalkyl include unsubstituted $(C_3-C_{20})$cycloalkyl, unsubstituted $(C_3-C_{10})$cycloalkyl, cyclopropyl, and cyclodecyl. Examples of substituted $(C_3-C_{40})$cycloalkyl are substituted $(C_3-C_{20})$cycloalkyl, substituted $(C_3-C_{10})$cycloalkyl, cyclopentanon-2-yl, and 1-fluorocyclohexyl.

Preferably, each hydrocarbylene independently has from 1 to 40 carbon atoms. Examples of $(C_1-C_{40})$hydrocarbylene are unsubstituted or substituted $(C_6-C_{40})$arylene, $(C_3-C_{40})$cycloalkylene, and $(C_1-C_{40})$alkylene (e.g., $(C_1-C_{20})$alkylene). In some embodiments, the diradicals are on a same carbon atom (e.g., —CH$_2$—) or on adjacent carbon atoms (i.e., 1,2-diradicals), or are spaced apart by one, two, etc., intervening carbon atoms (e.g., respective 1,3-diradicals, 1,4-diradicals, etc.). Preferred is a 1,2-, 1,3-, 1,4-, or an α-, ω-diradical, and more preferably a 1,2-diradical. The α-, ω-omega-diradical is a diradical that has a maximum carbon backbone spacing between the radical carbons. More preferred is a 1,2-diradical version of $(C_6-C_{18})$arylene, $(C_3-C_{20})$cycloalkylene, or $(C_2-C_{20})$alkylene; a 1,3-diradical version of $(C_6-C_{18})$arylene, $(C_4-C_{20})$cycloalkylene, or $(C_3-C_{20})$alkylene; or a 1,4-diradical version of $(C_6-C_{18})$arylene, $(C_6-C_{20})$cycloalkylene, or $(C_4-C_{20})$alkylene.

Preferably, each alkylene independently has from 1 to 40 carbon atoms. The term "$(C_1-C_{40})$alkylene" means a saturated straight chain or branched chain diradical (i.e., the radicals are not on ring atoms) of from 1 to 40 carbon atoms that is unsubstituted or substituted by at least one $R^S$. Other alkylene groups (e.g., $(C_1-C_{12})$alkylene)) are defined in an analogous manner. Examples of unsubstituted $(C_1-C_{40})$alkylene are unsubstituted $(C_1-C_{20})$alkylene, including unsubstituted 1,2-$(C_2-C_{10})$alkylene; 1,3-$(C_3-C_{10})$alkylene; 1,4-$(C_4-C_{10})$alkylene; —CH$_2$—, —CH$_2$CH$_2$—, —(CH$_2$)$_3$, —CH$_2\overset{|}{C}$CHCH$_3$, —(CH$_2$)$_4$—, —(CH$_2$)$_5$—, —(CH$_2$)$_6$—, —(CH$_2$)$_7$—, —(CH$_2$)$_8$—, and —(CH$_2$)$_4$C(H)(CH$_3$)—. Examples of substituted $(C_1-C_{40})$alkylene are substituted $(C_1-C_{20})$alkylene, —CF$_2$—, —C(O)—, and —(CH$_2$)$_{14}$C(CH$_3$)$_2$(CH$_2$)$_5$— (i.e., a 6,6-dimethyl substituted normal-1,20-eicosylene). Since as mentioned previously two $R^S$ may be taken together to form a $(C_1-C_{18})$alkylene, examples of substituted $(C_1-C_{40})$alkylene also include 1,2-bis(methylene)cyclopentane, 1,2-bis(methylene)cyclohexane, 2,3-bis(methylene)-7,7-dimethyl-bicyclo[2.2.1]heptane, and 2,3-bis(methylene)bicyclo[2.2.2]octane.

Preferably, each cycloalkylene independently has from 3 to 40 carbon atoms. The term "$(C_3-C_{40})$cycloalkylene" means a cyclic diradical (i.e., the radicals are on ring atoms) that is unsubstituted or substituted by at least one $R^S$. Examples of unsubstituted $(C_3-C_{40})$cycloalkylene are 1,3-cyclopropylene, 1,1-cyclopropylene, and 1,2-cyclohexylene. Examples of substituted $(C_3-C_{40})$cycloalkylene are 2-oxo-1,3-cyclopropylene and 1,2-dimethyl-1,2-cyclohexylene.

Preferably, each heterohydrocarbyl independently has from 1 to 40 carbon atoms. The term "$(C_1-C_{40})$heterohydrocarbyl" means a heterohydrocarbon radical and the term "$(C_1-C_{40})$heterohydrocarbylene" means a heterohydrocarbon diradical, and each heterohydrocarbon independently has at least one heteroatom B(R$^C$)O; S; S(O); S(O)$_2$; Si(R$^C$)$_2$; Ge(R$^C$)$_2$; P(R$^P$); and N(R$^N$), wherein independently each R$^C$ is unsubstituted $(C_1-C_{18})$hydrocarbyl, each R$^P$ is unsubstituted $(C_1-C_{18})$hydrocarbyl; and each R$^N$ is unsubstituted $(C_1-C_{18})$hydrocarbyl or absent (e.g., absent when N comprises —N= or tri-carbon substituted N). The radicals of the diradical can be on same or different type of atoms (e.g., both on saturated acyclic atoms or one on an acyclic atom and one on aromatic atom). Other heterohydrocarbyl (e.g., $(C_1-C_{12})$ heterohydrocarbyl)) and heterohydrocarbylene groups are defined in an analogous manner. Preferably, the heteroatom(s) is O; S; S(O); S(O)$_2$; Si(R$^C$)$_2$; P(R$^P$); or N(R$^N$). The heterohydrocarbon radical and each of the heterohydrocarbon diradicals independently is on a carbon atom or heteroatom thereof, although preferably each is on a carbon atom when bonded to a heteroatom in formula (I) or to a heteroatom of another heterohydrocarbyl or heterohydrocarbylene. Each $(C_1-C_{40})$heterohydrocarbyl and $(C_1-C_{40})$heterohydrocarbylene independently is unsubstituted or substituted (by at least one $R^S$), aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another.

Preferably, each heteroaryl independently has from 1 to 40 carbon atoms. The term "$(C_1-C_{40})$heteroaryl" means an unsubstituted or substituted (by at least one $R^S$) mono-, bi- or tricyclic heteroaromatic hydrocarbon radical of from 1 to 40 total carbon atoms and from 1 to 4 heteroatoms; from 1 to 44 total ring atoms, preferably from 5 to 10 total ring atoms, and the mono-, bi- or tricyclic radical comprises 1, 2 or 3 rings, respectively, wherein the 1-ring is heteroaromatic; at least one of the 2 or 3 rings is heteroaromatic; and the 2 or 3 rings independently are fused or non-fused. Other heteroaryl groups (e.g., $(C_1-C_{12})$heteroaryl)) are defined in an analogous manner. The monocyclic heteroaromatic hydrocarbon radical is a 5-membered or 6-membered ring. The 5-membered ring has from 1 to 4 carbon atoms and from 4 to 1 heteroatoms, respectively, each heteroatom being O, S, N, or P, and preferably O, S, or N. Examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 4 or 5 carbon atoms and 2 or 1 heteroatoms, the heteroatoms being N or P, and preferably N. Examples of 6-membered ring heteroaromatic hydrocarbon radical are pyridine-2-yl; pyrimidin-2-yl; and pyrazin-2-yl. The bicyclic heteroaromatic hydrocarbon radical preferably is a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical preferably is a fused 5,6,5-; 5,6,6-; 6,5,6-; or 6,6,6-ring system. An example of the fused 5,6,5-ring system is 1,7-dihydropyrrolo[3,2-f]indol-1-yl. An example of the fused 5,6,6-ring system is 1H-benzo[f]indol-1-yl. An example of the fused 6,5,6-ring system is 9H-carbazol-9-yl, which may also be named as a dibenzo-1H-pyrrole-1-yl. An example of the fused 6,5,6-ring system is 9H-carbazol-9-yl. An example of the fused 6,6,6-ring system is acrydin-9-yl. The 5-membered rings and 6-membered rings of the fused 5,6-; 6,6-; 5,6,5-; 5,6,6-; 6,5,6-; and 6,6,6-ring systems independently can be as described above for 5-membered and 6-membered rings, respectively, except where the ring fusions occur.

The aforementioned heteroalkyl and heteroalkylene groups are saturated straight or branched chain radicals or diradicals, respectively, containing at least one carbon atom and at least one heteroatom (up to 4 heteroatoms) $Si(R^C)_2$, $Ge(R^C)_2$, $P(R^P)$, $N(R^N)$, N, O, S, S(O), and $S(O)_2$ as defined above, wherein each of the heteroalkyl and heteroalkylene groups independently are unsubstituted or substituted by at least one $R^S$.

Unless otherwise indicated herein the term "heteroatom" means O, S, S(O), $S(O)_2$, $Si(R^C)_2$, $Ge(R^C)_2$, $P(R^P)$, or $N(R^N)$, wherein independently each $R^C$ is unsubstituted $(C_1-C_{18})$hydrocarbyl or the two $R^C$ are taken together to form a $(C_2-C_{19})$alkylene (e.g., the two $R^C$ together with the silicon atom to which they are both bonded form a 3-membered to 20-membered silacycloalkyl), each $R^P$ is unsubstituted $(C_1-C_{18})$hydrocarbyl; and each $R^N$ is unsubstituted $(C_1-C_{18})$hydrocarbyl, a hydrogen atom, or absent (absent when N comprises —N= as in a N-containing heteroaryl).

Preferably, there are no O—O, S—S, or O—S bonds, other than O—S bonds in an S(O) or $S(O)_2$ diradical functional group, in the metal-ligand complex of formula I. More preferably, there are no O—O, N—N, P—P, N—P, S—S, or O—S bonds, other than O—S bonds in an S(O) or $S(O)_2$ diradical functional group, in the metal-ligand complex of formula I.

The term "saturated" means lacking carbon-carbon double bonds, carbon-carbon triple bonds, and (in heteroatom-containing groups) carbon-nitrogen, carbon-phosphorus, and carbon-silicon double bonds. Where a saturated chemical group is substituted by one or more substituents $R^S$, one or more double and/or triple bonds optionally may or may not be present in substituents $R^S$. The term "unsaturated" means containing one or more carbon-carbon double bonds, carbon-carbon triple bonds, and (in heteroatom-containing groups) carbon-nitrogen, carbon-phosphorus, and carbon-silicon double bonds, not including any such double bonds that may be present in substituents $R^S$, if any, or in (hetero)aromatic rings, if any.

In the metal-ligand complex of formula (I) certain variables and chemical groups n, M, X, Z, L, $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$, and $R^{8d}$, as the formulas allow, are preferred. Examples of such preferred groups follow.

Preferably M is zirconium or hafnium. The formal oxidation state of M may vary as +2 or +4. Any combination of a preferred M and a preferred formal oxidation state may be employed.

In various embodiments n may be 0, 1, 2, or 3.

Certain X groups are preferred. In some embodiments each X independently is the monodentate ligand. Preferably when there are two or more X monodentate ligands, each X is the same. In some embodiments the monodentate ligand is the monoanionic ligand. The monoanionic ligand has a net formal oxidation state of −1. Each monoanionic ligand preferably independently is hydride, hydrocarbyl carbanion, heterohydrocarbyl carbanion, halide, nitrate, carbonate, phosphate, sulfate, $HC(O)O^-$, hydrocarbylC(O)$O^-$, HC(O)$N(H)^-$, hydrocarbylC(O)N(H)$^-$, hydrocarbylC(O)N-($C_1$-$C_{20}$)hydrocarbyl)$^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, hydrocarbyl, or heterohydrocarbyl, or $R^K$ and $R^L$ are taken together to form a $(C_2-C_{40})$ hydrocarbylene or heterohydrocarbylene and $R^M$ is as defined above.

In some embodiments at least one monodentate ligand of X independently is the neutral ligand. Preferably the neutral ligand is a neutral Lewis base group that is $R^X NR^K R^L$, $R^K OR^L$, $R^K SR^L$, or $R^X PR^K R^L$, wherein each $R^X$ independently is hydrogen, hydrocarbyl, $[(C_1-C_{10})hydrocarbyl]_3Si$, $[(C_1-C_{10})hydrocarbyl]_3Si(C_1-C_{10})hydrocarbyl$, or heterohydrocarbyl and each $R^K$ and $R^L$ independently is as defined above.

In some embodiments, each X is a monodentate ligand that independently is a halogen atom, unsubstituted $(C_1-C_{20})$hydrocarbyl, unsubstituted $(C_1-C_{20})$hydrocarbylC(O)O—, or $R^K R^L N$— wherein each of $R^K$ and $R^L$ independently is an unsubstituted $(C_1-C_{20})$hydrocarbyl. In some embodiments each monodentate ligand X is a chlorine atom, $(C_1-C_{10})$hydrocarbyl (e.g., $(C_1-C_6)$alkyl or benzyl), unsubstituted $(C_1-C_{10})$hydrocarbylC(O)O—, or $R^K R^L N$— wherein each of $R^K$ and $R^L$ independently is an unsubstituted $(C_1-C_{10})$hydrocarbyl.

In some embodiments there are at least two X and the two X are taken together to form the bidentate ligand. In some embodiments the bidentate ligand is a neutral bidentate ligand. Preferably the neutral bidentate ligand is a diene of formula $(R^D)_2C=C(R^D)-C(R^D)=C(R^D)_2$, wherein each $R^D$ independently is H, unsubstituted $(C_1-C_6)$alkyl, phenyl, or naphthyl. In some embodiments the bidentate ligand is a monoanionic-mono(Lewis base) ligand. The monoanionic-mono(Lewis base) ligand preferably is a 1,3-dionate of formula (D): $R^E-C(O^-)=CH-C(=O)-R^E$ (D), wherein each $R^D$ independently is H, unsubstituted $(C_1-C_6)$alkyl, phenyl, or naphthyl. In some embodiments the bidentate ligand is a dianionic ligand. The dianionic ligand has a net formal oxidation state of −2. Preferably each dianionic ligand independently is carbonate, oxalate (i.e., $^-O_2CC(O)O^-$), $(C_2-C_{40})$hydrocarbylene dicarbanion, heterohydrocarbylene dicarbanion, phosphate, or sulfate.

As previously mentioned, number and charge (neutral, monoanionic, dianionic) of X are selected depending on the formal oxidation state of M such that the metal-ligand complex of formula (I) is, overall, neutral.

In some embodiments each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments n is 2 and each X is the same.

In some embodiments at least two X are different. In some embodiments n is 2 and each X is a different one of methyl; ethyl; 1-propyl; 2-propyl; 1-butyl; 2,2,-dimethylpropyl; trimethylsilylmethyl; phenyl; benzyl; and chloro.

The integer n indicates number of X. Preferably n is 2 or 3 and at least two X independently are monoanionic monodentate ligands and a third X, if present, is a neutral monodentate ligand. In some embodiments n is 2 at two X are taken together to form a bidentate ligand. In some embodiments the bidentate ligand is 2,2-dimethyl-2-silapropane-1,3-diyl or 1,3-butadiene.

In some embodiments L is two-carbon atom hydrocarbylene. In some embodiments L comprises the 2-carbon atom linker backbone (e.g., L is $-CH_2CH_2-$, $-CH=CH-$ or $-CH(CH_3)CH(CH_3)-$). In some embodiments L is the unsubstituted alkylene, and more preferably L is an acyclic unsubstituted alkylene, and still more preferably the acyclic unsubstituted alkylene is $-CH_2CH_2-$, $-CH_2CH(CH_2)-$, cis-$CH(CH_3)CH(CH_3)-$, trans-$CH(CH_3)CH(CH_3)-$.

In some embodiments L is the unsubstituted 1,2-cycloalkylene, and more preferably L is 1,2-cyclopentane-diyl or 1,2-cyclohexane-diyl. In some embodiments L is the substituted cycloalkylene. In other embodiments L is substituted or unsubstituted 1,2-arylene or 1,2-heteroarylene (e.g., L is 1,2-phenylene-, 2,3-naphthalene or 2,3-pyridyl). In still other embodiments L is substituted or unsubstituted two-atom heterohydrocarbylene. In some embodiments L comprises the 2-atom linker backbone (e.g., L is $-CH_2CH(OCH_3)-$ or $-CH_2Si(CH_3)_2-$).

Certain $R^{1a}$, $R^{2a}$, $R^{1b}$, and $R^{2b}$ groups are preferred. In some embodiments one of $R^{1a}$, $R^{2a}$, $R^{1b}$, and $R^{2b}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$, halogen atom; and each of the others of $R^{1a}$, $R^{2a}$, $R^{1b}$, and $R^{2b}$ is a hydrogen atom. In some such embodiments it is each of $R^{2a}$, $R^{1b}$, and $R^{2b}$ that is a hydrogen atom. In other such embodiments it is each of $R^{1a}$, $R^{1b}$, and $R^{2b}$ that is a hydrogen atom.

In some embodiments two of $R^{1a}$, $R^{2a}$, $R^{1b}$, and $R^{2b}$ independently are a hydrocarbyl, heterohydrocarbyl, or halogen atom; and each of the others of $R^{1a}$, $R^{2a}$, $R^{1b}$, and $R^{2b}$ is a hydrogen atom. In some such embodiments it is each of $R^{1b}$ and $R^{2b}$ that is a hydrogen atom. In other such some embodiments it is each of $R^{2a}$ and $R^{2b}$ that is a hydrogen atom. In still other such some embodiments it is each of $R^{1a}$ and $R^{1b}$ that is a hydrogen atom.

In some embodiments three of $R^{1a}$, $R^{2a}$, $R^{1b}$, and $R^{2b}$ independently are a hydrocarbyl, heterohydrocarbyl, or halogen atom; and the other of $R^{1a}$, $R^{2a}$, $R^{1b}$, and $R^{2b}$ is a hydrogen atom. In some such embodiments it is $R^{1b}$ that is a hydrogen atom. In other such embodiments it is $R^{2b}$ that is a hydrogen atom.

In some embodiments each of $R^{1a}$, $R^{2a}$, $R^{1b}$, and $R^{2b}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom.

In some embodiments one of $R^{1a}$ and $R^{1b}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$, halogen atom, and the other of $R^{1a}$ and $R^{1b}$ independently is a hydrogen atom, a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom. In some embodiments one of $R^{1a}$ and $R^{1b}$ independently is a hydrocarbyl, heterohydrocarbyl or halogen atom, and the other of $R^{1a}$ and $R^{1b}$ independently is a hydrogen atom, hydrocarbyl, heterohydrocarbyl, or halogen atom. In some embodiments each of $R^{1a}$ and $R^{1b}$ independently is a hydrocarbyl or halogen atom. In some embodiments at least one of $R^{1a}$ and $R^{1b}$ is hydrocarbyl. In some embodiments at least one of $R^{1a}$ and $R^{1b}$ is halogen atom.

In some embodiments one of $R^{2a}$ and $R^{2b}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom, and the other of $R^{2a}$ and $R^{2b}$ independently is a hydrogen atom, $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom. In some embodiments one of $R^{2a}$ and $R^{2b}$ independently is a hydrocarbyl, heterohydrocarbyl or halogen atom, and the other of $R^{2a}$ and $R^{2b}$ independently is a hydrogen atom, hydrocarbyl, heterohydrocarbyl, or halogen atom. In some embodiments each of $R^{2a}$ and $R^{2b}$ independently is a hydrocarbyl or halogen atom. In some embodiments at least one of $R^{2a}$ and $R^{2b}$ is hydrocarbyl. In some embodiments at least one of $R^{2a}$ and $R^{2b}$ is halogen atom.

Certain combinations of $R^{1a}$, $R^{1b}$, $R^{2a}$, and $R^{2b}$ are preferred. In some embodiments each of $R^{1a}$ and $R^{1b}$ is $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$, halogen atom; and preferably each of $R^{2a}$ and $R^{2b}$ is a hydrogen, $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom.

In some embodiments each of $R^{1a}$ and $R^{1b}$ is $(C_1-C_{40})$hydrocarbyl, $(C_1-C_{40})$heterohydrocarbyl, halogen atom; and preferably each of $R^{2a}$ and $R^{2b}$ is a hydrogen, $(C_1-C_{40})$hydrocarbyl, $(C_1-C_{40})$heterohydrocarbyl or halogen atom.

In some embodiments at least three of $R^{1a}$, $R^{1b}$, $R^{2a}$, and $R^{2b}$ independently is a hydrocarbyl, heterohydrocarbyl, or halogen atom; and the remaining one of $R^{1a}$, $R^{1b}$, $R^{2a}$, and $R^{2b}$ independently is a hydrogen atom, hydrocarbyl, heterohydrocarbyl, or halogen atom. In some embodiments at least three and in other embodiments each of $R^{1a}$, $R^{1b}$, $R^{2a}$, and $R^{2b}$ independently is a hydrocarbyl or halogen atom.

In some embodiments $R^{1a}$ is a hydrogen atom; $R^{1b}$ is a hydrocarbyl, heterohydrocarbyl, or halogen atom; $R^{2a}$ independently is a hydrocarbyl, heterohydrocarbyl, or halogen atom; and $R^{2b}$ independently is a hydrogen atom, hydrocarbyl, heterohydrocarbyl, or halogen atom. In some embodiments $R^{1b}$ independently is hydrocarbyl or halogen atom.

In some embodiments each of $R^{1a}$ and $R^{1b}$ is a hydrogen atom; and at least one, and preferably each of $R^{2a}$ and $R^{2b}$ independently is a hydrocarbyl, heterohydrocarbyl, or halogen atom. In some embodiments at least one and preferably each of the $R^{2a}$ and $R^{2b}$ independently is hydrocarbyl or halogen atom. Certain combinations of $R^{2a}$, $R^{2b}$, $R^{3a}$, and $R^{3b}$ are preferred. In some embodiments $R^{2a}$ is a hydrogen atom; $R^{2b}$ is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom; $R^{3a}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom; and $R^{3b}$ independently is a hydrogen atom, $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$ or halogen atom. In some embodiments $R^{2b}$ independently is hydrocarbyl or halogen atom.

Certain combinations of $R^{2a}$, $R^{2b}$, $R^{3a}$, and $R^{3b}$ are preferred. In some embodiments $R^{2a}$ is a hydrogen atom; $R^{2b}$ is a hydrocarbyl, heterohydrocarbyl, or halogen atom; $R^{3a}$ independently is a hydrocarbyl, heterohydrocarbyl, or halogen atom; and $R^{3b}$ independently is a hydrogen atom, hydrocarbyl, heterohydrocarbyl, or halogen atom. In some embodiments $R^{2b}$ independently is hydrocarbyl or halogen atom.

Certain combinations of $R^{1a}$, $R^{1b}$, $R^{2a}$, $R^{2b}$, $R^{3a}$, and $R^{3b}$ are more preferred. In some embodiments $R^{2a}$ and $R^{2b}$ are each hydrogen atom and $R^{1a}$, $R^{1b}$, $R^{3a}$, and $R^{3b}$ independently is hydrocarbyl, heterohydrocarbyl, or halogen atom; and more preferably $R^{2a}$ and $R^{2b}$ are each hydrogen atom and each of $R^{1a}$ and $R^{1b}$ independently is $(C_1-C_6)$hydrocarbyl, $(C_1-C_5)$heterohydrocarbyl, fluorine atom, or chlorine atom, and each of $R^{3a}$, and $R^{3b}$ independently is $(C_1-C_{12})$hydrocarbyl, $(C_1-C_{11})$heterohydrocarbyl, fluorine atom, chlorine atom, or bromine atom. In some embodiments $R^{1a}$ and $R^{1b}$ are each hydrogen atom; each of $R^{2a}$ and $R^{2b}$ independently is $(C_1-C_8)$hydrocarbyl, $(C_1-C_7)$heterohydrocarbyl, fluorine atom, chlorine atom, or bromine atom; and each of $R^{3a}$, and $R^{3b}$ independently is $(C_1-C_{12})$hydrocarbyl, $(C_1-C_{11})$heterohydrocarbyl, fluorine atom, chlorine atom, or bromine atom.

Preferably each hydrocarbyl, whenever used to define $R^{1a}$ or $R^{1b}$, independently is an alkyl or cycloalkyl. Preferably the alkyl is $(C_1-C_{12})$alkyl, more preferably $(C_1-C_8)$alkyl, still more preferably $(C_1-C_6)$alkyl, and even more preferably $(C_1-C_4)$alkyl. Preferably the cycloalkyl is $(C_3-C_6)$cycloalkyl, and more preferably $(C_3-C_4)$cycloalkyl. Preferably the $(C_3-C_4)$cycloalkyl is cyclopropyl. Preferably the $(C_1-C_4)$alkyl is methyl, ethyl, 1-propyl, 2-propyl, 1-butyl, 2-butyl, 2-methylpropyl, or 1,1-dimethylethyl, and more preferably methyl, ethyl, 2-propyl, or 1,1-dimethylethyl. In some embodiments the $(C_1-C_4)$alkyl is ethyl, 2-propyl, or 1,1-dimethylethyl. Preferably each halogen atom, whenever used to define $R^{1a}$, $R^{1b}$, $R^{2a}$, $R^{2b}$, $R^{3a}$, and $R^{3b}$, independently is a fluorine atom, chlorine atom, bromine atom or iodine atom.

In some embodiments each of $R^{1a}$, $R^{1b}$, $R^{3a}$, and $R^{3b}$ independently is methyl; ethyl; 2-propyl; 1,1-dimethylethyl; mono-, di-, or trifluoromethyl; methoxy; ethoxy; 1-methylethoxy; mono-, di-, or trifluoromethoxy; halogen atom; cyano; nitro; dimethylamino; aziridin-1-yl; or cyclopropyl. In some embodiments at least one, and in some embodiments each of $R^{2a}$ and $R^{2b}$ is a hydrogen atom and each of $R^{1a}$, $R^{1b}$, $R^{3a}$, and $R^{3b}$ independently is methyl; ethyl; 1-propyl; 2-propyl; 1-butyl; 1,1-dimethylethyl; cyano; dimethylamino; methoxy; trifluoromethyl; bromine atom; fluorine atom, or chlorine atom.

In some embodiments of the metal-ligand complex of formula (I) each of $R^{1a}$ and $R^{1b}$ is a hydrogen atom and at least one, and in some embodiments each of $R^{2a}$, $R^{2b}$, $R^{3a}$, and $R^{3b}$ independently is methyl; ethyl; 2-propyl; 1,1-dimethylethyl; mono-, di-, or trifluoromethyl; methoxy; ethoxy; 1-methylethoxy; mono-, di-, or trifluoromethoxy; halogen atom; cyano; nitro; dimethylamino; aziridin-1-yl; or cyclopropyl. In some embodiments at least one, and in some embodiments each of $R^{1a}$ and $R^{1b}$ is a hydrogen atom and each of $R^{2a}$, $R^{2b}$, $R^{3a}$, and $R^{3b}$ independently is methyl; ethyl; 1-propyl; 2-propyl; 1-butyl; 1,1-dimethylethyl; cyano; dimethylamino; methoxy; trifluoromethyl; bromine atom; fluorine atom, or chlorine atom.

In some embodiments in the metal-ligand complex of formula (I) one of $R^{1a}$ and $R^{1b}$ is methyl; the other of $R^{1a}$ and $R^{1b}$ is as in any one of the preferred embodiments described herein. More preferably in some of such embodiments each of $R^{2a}$ and $R^{2b}$ is a hydrogen atom and each of $R^{3a}$ and $R^{3b}$ independently is as in any one of the preferred embodiments described herein.

In some embodiments in the metal-ligand complex of formula (I) at least one, and more preferably each of $R^{1a}$ and $R^{1b}$ independently is ethyl; 2-propyl; mono-, di-, or trifluoromethyl; methoxy; ethoxy; 1-methylethoxy; mono-, di-, or trifluoromethoxy; halogen atom; cyano; nitro; dimethylamino; aziridin-1-yl; or cyclopropyl. More preferably in such embodiments at least one, and more preferably each of $R^{2a}$ and $R^{2b}$, is a hydrogen atom and each of $R^{3a}$ and $R^{3b}$ independently is as in any one of the preferred embodiments described herein. In some of such embodiments preferably at least one, and more preferably each of $R^{1a}$ and $R^{1b}$, is a halogen atom or $(C_1-C_6)$alkyl, and still more preferably a $(C_1-C_4)$alkyl, fluorine or chlorine atom. In some embodiments at least one, and preferably each of $R^{1a}$ and $R^{1b}$, is the fluorine atom. In some embodiments at least one, and preferably each of $R^{1a}$ and $R^{1b}$, is the chlorine atom. In some embodiments at least one, and preferably each of $R^{1a}$ and $R^{1b}$, is $(C_1-C_4)$alkyl, and more preferably methyl. In general any combination of $R^{1a}$ and $R^{1b}$, $R^{2a}$ and $R^{2b}$, and $R^{3a}$ and $R^{3b}$ may be made, within the selections provided, enabled, or exemplified.

In some embodiments of the metal-ligand complex of formula (I) or the ligand of formula (Q), at least one of $R^{1a}$, $R^{1b}$, $R^{3a}$, $R^{3b}$, $R^{7c}$, and $R^{7d}$ is not methyl. In some embodiments of the metal-ligand complex of formula (I) at least one of $R^{7c}$, $R^{7d}$, $R^{3a}$, and $R^{3b}$ is not methyl.

Certain $R^{4a}$ and $R^{4b}$ are preferred. In some embodiments each of $R^{4a}$ and $R^{4b}$ is a hydrogen atom. In some embodiments at least one and in some embodiments each of $R^{4a}$ and $R^{4b}$ independently is as defined previously for $R^{1a}$ and $R^{1b}$, respectively. When $R^{4a}$ or $R^{4b}$ independently is as defined previously for $R^{1a}$, or $R^{1b}$, respectively, or both, $R^{4a}$ and $R^{1a}$ independently may be the same or different and $R^{4b}$ and $R^{1b}$ independently may be the same or different. In some embodiments at least one, and in some embodiments each of $R^{4a}$ and $R^{4b}$ independently is methyl; ethyl; 1-propyl; 2-propyl; 1-butyl; 1,1-dimethylethyl; cyano; dimethylamino; methoxy; trifluoromethyl; bromine atom; fluorine atom, or chlorine atom.

Certain $R^{5c}$ and $R^{5d}$ are preferred. In some embodiments $R^{5c}$ and $R^{5d}$ are the same as each other. In some embodiments $R^{5c}$ and $R^{5d}$ are different from each other.

In some embodiments at least one, and more preferably each of $R^{5c}$ and $R^{5d}$ independently is $(C_6-C_{40})$aryl. Preferably the $(C_6-C_{40})$aryl is a $(C_6-C_{18})$aryl and more preferably $(C_6-C_{12})$aryl. In some embodiments the $(C_6-C_{40})$aryl is a substituted phenyl and preferably a 2,4-disubstituted phenyl wherein each substituent is $R^S$, 2,5-disubstituted phenyl wherein each substituent is $R^S$; or 2,6-disubstituted phenyl wherein each substituent is $R^S$; and more preferably wherein each $R^S$ independently is phenyl, methyl, ethyl, isopropyl, or tertiary-butyl, and still more preferably 2,6-dimethylphenyl or 2,6-diisopropylphenyl. In some embodiments the ($C_6$-$C_{40}$)aryl is a 3,5-disubstituted phenyl wherein each substituent is $R^S$, and more preferably wherein each $R^S$ independently is phenyl, methyl, ethyl isopropyl, or tertiary-butyl, and still more preferably 3,5-di(tertiary-butyl)phenyl or 3,5-diphenylphenyl. In some embodiments the ($C_6$-$C_{40}$)aryl is a 2,4,6-trisubstituted phenyl wherein each substituent is $R^S$, and more preferably wherein each $R^S$ independently is phenyl, methyl, isopropyl, or tertiary-butyl; In some embodiments the ($C_6$-$C_{40}$)aryl is a naphthyl or substituted naphthyl wherein each substituent is $R^S$, and more preferably wherein each $R^S$ independently is phenyl, methyl, ethyl, isopropyl, or tertiary-butyl, and still more preferably 1-naphthyl, 2-methyl-1-naphthyl, or 2-naphthyl. In some embodiments the ($C_6$-$C_{40}$)aryl is a 1,2,3,4-tetrahydronaphthyl, and more preferably 1,2,3,4-tetrahydronaphth-5-yl or 1,2,3,4-tetrahydronaphth-6-yl. In some embodiments the ($C_6$-$C_{40}$) aryl is an anthracenyl, and more preferably anthracen-9-yl. In some embodiments the ($C_6$-$C_{40}$)aryl is a 1,2,3,4-tetrahydro-anthracenyl, and more preferably 1,2,3,4-tetrahydroanthracen-9-yl. In some embodiments the ($C_6$-$C_{40}$)aryl is a 1,2,3,4,5,6,7,8-octahydroanthracenyl, and more preferably 1,2,3,4,5,6,7,8-octahydroanthracen-9-yl, In some embodiments the ($C_6$-$C_{40}$)aryl is a phenanthrenyl, and more preferably a phenanthren-9-yl. In some embodiments the ($C_6$-$C_{40}$)aryl is a 1,2,3,4,5,6,7,8-octahydrophenanthrenyl, and more preferably 1,2,3,4,5,6,7,8-octahydro-phenanthren-9-yl. As mentioned before, each of the aforementioned ($C_6$-$C_{40}$)aryl independently is unsubstituted or substituted by one or more substituents $R^S$. In some embodiments the ($C_6$-$C_{40}$)aryl is unsubstituted. Preferred unsubstituted ($C_6$-$C_{40}$)aryl is unsubstituted inden-6-yl; 2,3-dihydro-1H-inden-6-yl; naphthalene-2-yl; or 1,2,3,4-tetrahydronaphthalen-6-yl; and more preferably unsubstituted naphthalen-1-yl; 1,2,3,4-tetrahydronaphthalen-5-yl; anthracen-9-yl; 1,2,3,4-tetrahydroanthracen-9-yl; or 1,2,3,4,5,6,7,8-octahydroanthracen-9-yl. As mentioned for ($C_6$-$C_{40}$)aryl hereinabove, each of the aforementioned ($C_6$-$C_{40}$)aryl independently is unsubstituted or substituted by one or more substituents $R^S$. In some embodiments the ($C_6$-$C_{40}$)aryl is substituted by from 1 or 4 $R^S$, wherein $R^S$ is as described previously. Preferably there are 1 or 2 $R^S$ substituents in each substituted ($C_6$-$C_{40}$), and more preferably 2 $R^S$ substituents in each substituted phenyl. Preferably each $R^S$ of the substituted ($C_6$-$C_{40}$)aryl of $R^{5c}$ and $R^{5d}$ independently is an unsubstituted ($C_3$-$C_{10}$)hydrocarbyl, more preferably an unsubstituted ($C_4$-$C_8$)hydrocarbyl, still more preferably phenyl or an unsubstituted ($C_4$-$C_{10}$)alkyl, and even more preferably an unsubstituted tertiary ($C_4$-$C_8$)alkyl (e.g., tertiary-butyl or tertiary-octyl (i.e., 1,1-dimethylhexyl)). Examples of preferred substituted ($C_6$-$C_{40}$)aryl are a 2,6-disubstituted-phenyl having same substituent $R^S$ (e.g., 2,6-dimethylphenyl; 2,6-diethylphenyl; 2,6-bis(1-methylethyl)phenyl; and 2,6-diphenyl-phenyl); a 3,5-disubstituted-phenyl having same substituent $R^S$ (e.g., 3,5-dimethylphenyl; 3,5-bis(trifluoromethyl)phenyl; 3,5-bis(1-methylethyl)phenyl; and 3,5-bis(1,1-dimethylethyl)phenyl; and 3,5-diphenyl-phenyl); 2,4,6-trisubstituted-phenyl having same substituent $R^S$ (e.g., 2,4,6-trimethylphenyl; and 2,4,6-tris(1-methylethyl)phenyl); 1-methyl-2,3-dihydro-1H-inden-6-yl; 1,1-dimethyl-2,3-dihydro-1H-inden-6-yl; 1-methyl-1,2,3,4-tetrahydronaphthalen-5-yl; and 1,1-dimethyl-1,2,3,4-tetrahydronaphthalen-5-yl.

In some embodiments at least one, and more preferably each of $R^{5c}$, and $R^{5d}$ independently is heteroaryl. Preferably the heteroaryl has at least one nitrogen atom-containing aromatic ring. More preferably the heteroaryl is a pyridinyl, indolyl, indolinyl, quinolinyl, 1,2,3,4-tetrahydroquinolinyl, isoquinolinyl, 1,2,3,4-tetrahydroisoquinolinyl, carbazolyl, 1,2,3,4-tetrahydrocarbazolyl, or 1,2,3,4,5,6,7,8-octahydrocarbazolyl. In some embodiments the heteroaryl is carbazolyl or a substituted carbazolyl, preferably a 2,7-disubstituted carbazolyl or 3,6-disubstituted carbazolyl, and more preferably 2,7-disubstituted 9H-carbazol-9-yl or 3,6-disubstituted 9H-carbazol-9-yl, wherein each substituent is $R^S$, more preferably wherein each $R^S$ independently is phenyl, methyl, ethyl, isopropyl, or tertiary-butyl, still more preferably 3,6-di(tertiary-butyl)-carbazolyl, 3,6-di(tertiary-octyl)-carbazolyl, 3,6-diphenylcarbazolyl, or 3,6-bis(2,4,6-trimethylphenyl)-carbazolyl, and more preferably 3,6-di(tertiary-butyl)-carbazol-9-yl, 3,6-di(tertiary-octyl)-carbazol-9-yl, 3,6-diphenylcarbazol-9-yl, or 3,6-bis(2,4,6-trimethylphenyl)-carbazol-9-yl. Examples of 2,7-disubstituted carbazolyl are the foregoing 3,6-disubstituted carbazolyl where the 3,6-substituents are moved to 2,7-positions, respectively. Tertiary-octyl is 1,1-dimethylhexyl. In some embodiments the heteroaryl is 1,2,3,4-tetrahydrocarbazolyl, preferably a 1,2,3,4-tetrahydrocarbazol-9-yl. As mentioned before for heteroaryl, each of the aforementioned heteroaryl independently is unsubstituted or substituted by one or more substituents $R^S$. Preferably each of the indolyl, indolinyl, and tetrahydro- and octahydro-containing heteroaryl is bonded via its ring nitrogen atom to the phenyl rings bearing $R^{5c}$, or $R^{5d}$ in formula (I). In some embodiments the heteroaryl is unsubstituted. Preferred unsubstituted heteroaryl is unsubstituted quinolin-4-yl, quinolin-5-yl, or quinolin-8-yl, (the quinolinyl N being at position 1); 1,2,3,4-tetrahydroquinolin-1-yl (the tetrahydroquinolinyl N being at position 1); isoquinolin-1-yl, isoquinolin-4-yl, isoquinolin-5-yl, or isoquinolin-8-yl (the isoquinolinyl N being at position 2); 1,2,3,4-tetrahydroisoquinolin-2-yl (the tetrahydroisoquinolinyl N being at position 2); 1H-indol-1-yl (the indolyl N being at position 1); 1H-indolin-1-yl (the indolinyl N being at position 1); 9H-carbazol-9-yl (the carbazolyl N being at position 9), which may also be named as a dibenzo-1H-pyrrole-1-yl; 1,2,3,4-tetrahydrocarbazolyl-9-yl (the tetrahydrocarbazolyl N being at position 9); or 1,2,3,4,5,6,7,8-octahydrocarbazolyl-9-yl (the octahydrocarbazolyl N being at position 9). In some embodiments the heteroaryl is substituted by from 1 or 4 $R^S$. Preferably there are 1 or 2 $R^S$ substituents in each substituted heteroaryl. Preferably each $R^S$ of the substituted heteroaryl of $R^{5c}$ and $R^{5d}$ independently is an unsubstituted ($C_3$-$C_{10}$)hydrocarbyl, more preferably an unsubstituted ($C_4$-$C_8$)hydrocarbyl, still more preferably phenyl or an unsubstituted ($C_4$-$C_{10}$)alkyl, and even more preferably an unsubstituted tertiary ($C_4$-$C_8$)alkyl (e.g., tertiary-butyl or tertiary-octyl (i.e., 1,1-dimethylhexyl)). Preferably the substituted heteroaryl is a 2,7-disubstituted quinolin-4-yl, 2,7-disubstituted quinolin-5-yl, or 3,6-disubstituted quinolin-8-yl; 3,6-disubstituted 1,2,3,4-tetrahydroquinolin-1-yl; 4-monosubstituted isoquinolin-5-yl; 2-monosubstituted 1,2,3,4-tetrahydroisoquinolin-2-yl; 3-monosubstituted 1H-indol-1-yl; 3-monosubstituted 1H-indolin-1-yl; 2,7-disubstituted 9H-carbazol-9-yl; 3,6-disubstituted 9H-carbazol-9-yl; 3,6-disubstituted 1,2,3,4-tetrahydrocarbazolyl-9-yl; or 3,6-disubstituted 1,2,3,4,5,6,7,8-octahydrocarbazolyl-9-yl.

Examples of preferred substituted heteroaryl are 4,6-bis(1,1-dimethylethyl)pyridine-2-yl; 4,6-diphenylpyridin-2-yl; 3-phenyl-1H-indol-1-yl; 3-(1,1-dimethylethyl)-1H-indol-1-yl; 3,6-diphenyl-9H-carbazol-9-yl; 3,6-bis[2',4',6'-tris(1,1-dimethylphenyl)]-9H-carbazol-9-yl; and more preferably each of $R^{5c}$ and $R^{5d}$ is 3,6-bis(1,1-dimethylethyl)-9H-carbazol-9-yl. The term "tertiary butyl" means 1,1-dimethylethyl. More preferably $R^{5c}$ and $R^{5d}$ are defined as in any one of the Examples described later.

In some embodiments of the metal-ligand complex of formula (I) each Z is O, each of $R^{2a}$ and $R^{2b}$ is a hydrogen atom, and each of $R^{5c}$ and $R^{5d}$ independently is the heteroaryl. More preferred in such embodiments is a metal-ligand complex of any one of formulas (Ia) to (Ie):

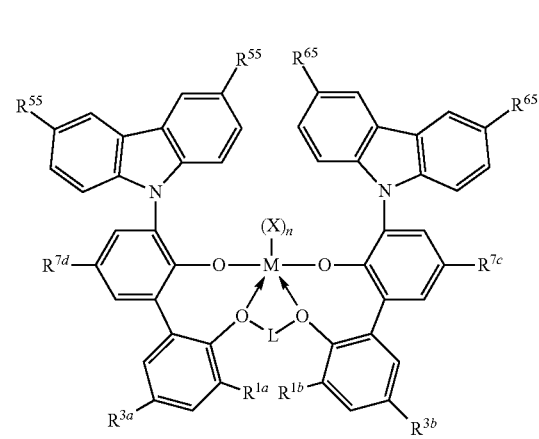

(Ia)

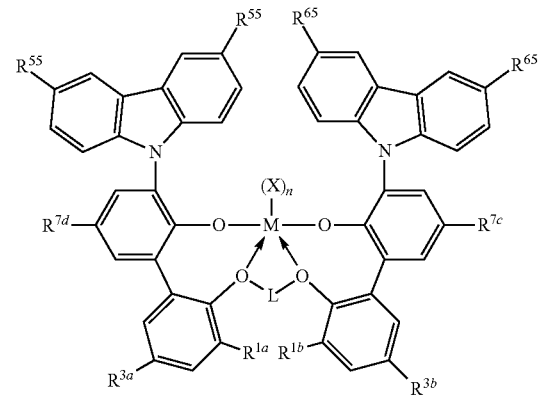

(Ib)

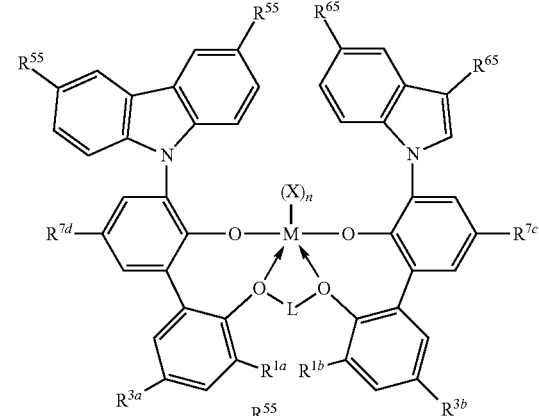

(Ic)

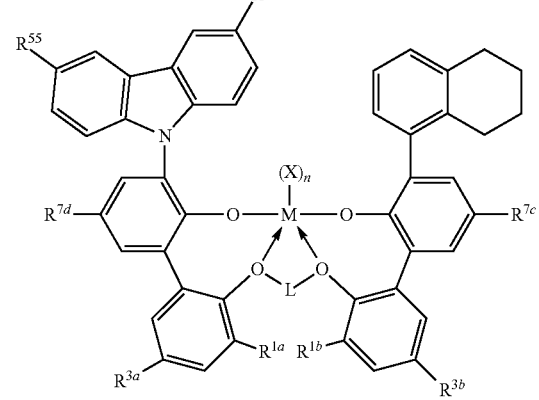

-continued

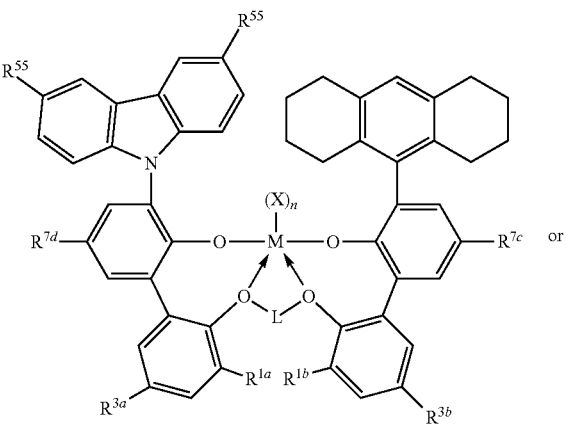

(Id)

(Ie)

wherein M, X, $R^{1a}$, $R^{1b}$, $R^{3a}$, $R^{3b}$, $R^{7c}$, $R^{7d}$, and L are as defined previously and each $R^{55}$ and $R^{65}$ is as defined previously. Preferably each $R^{55}$ and $R^{65}$ independently is a hydrogen atom or an unsubstituted $(C_1-C_{12})$alkyl.

In some embodiments the metal-ligand complex of formula (I) each Z is O, each of $R^{1a}$, and $R^{1b}$ is a hydrogen atom, and each of $R^{5c}$ and $R^{5d}$ independently is the heteroaryl. More preferred in such embodiments is a metal-ligand complex of any one of formulas (If) to (Ij):

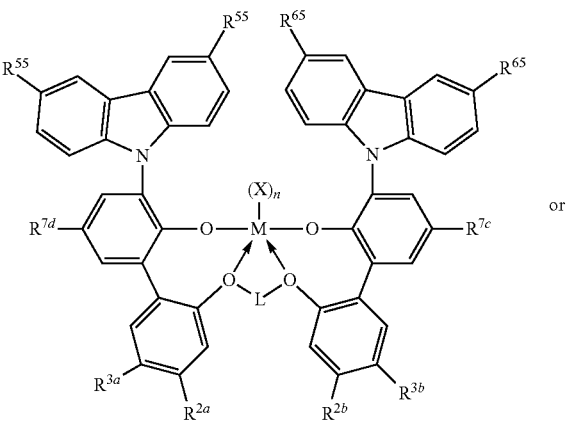

(If)

(Ig)
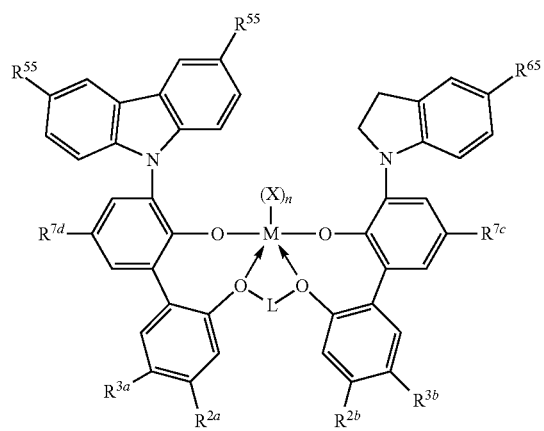

(Ih)
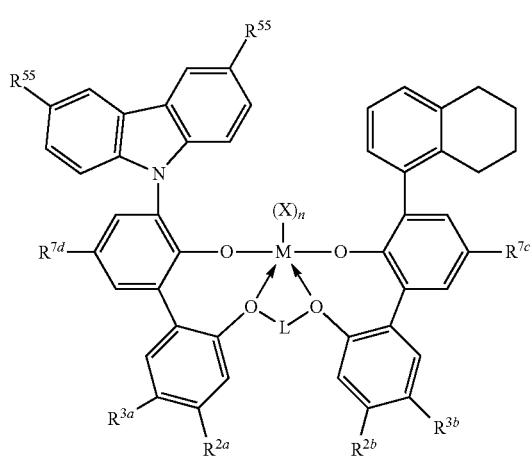

(Ii)
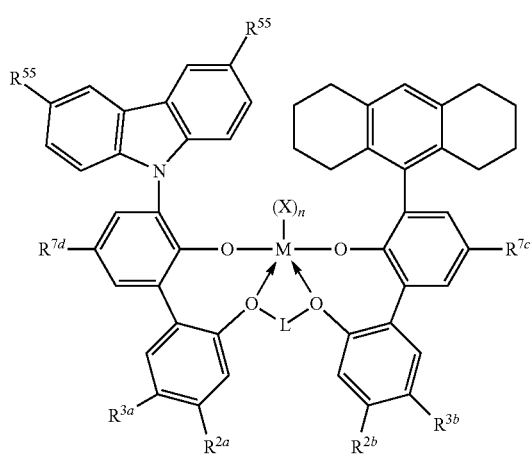

(Ij)
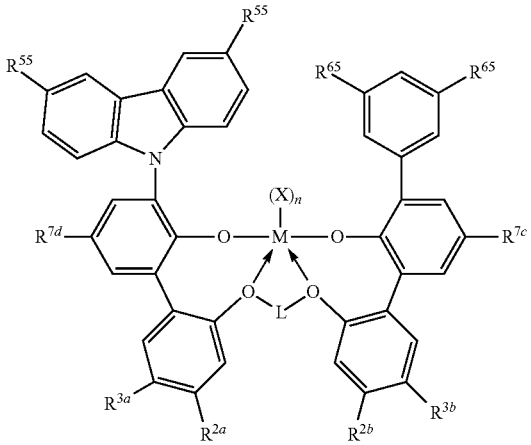

wherein M, X, $R^{2a}$, $R^{2b}$, $R^{3a}$, $R^{3b}$, $R^{7c}$, $R^{7d}$, and L are as defined previously and each $R^{55}$ and $R^{65}$ is as defined previously. Preferably each $R^{55}$ and $R^{65}$ independently is a hydrogen atom or an unsubstituted $(C_1-C_{12})$alkyl.

In some embodiments the metal-ligand complex of formula (I) each Z is O, each of $R^{2a}$ and $R^{2b}$ is a hydrogen atom, and each of $R^{5c}$ and $R^{5d}$ independently is the $(C_6-C_{40})$aryl. More preferred in such embodiments is a metal-ligand complex of any one of formulas (Ik) to (Io):

(Ik)
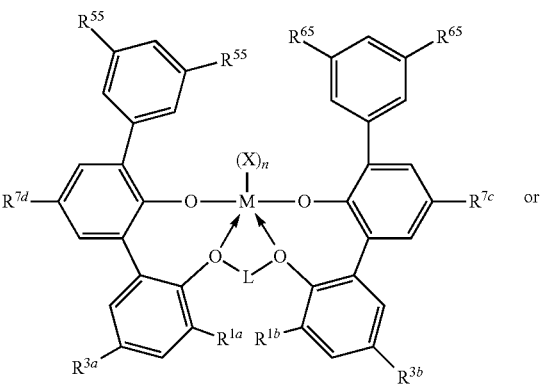

(Il)
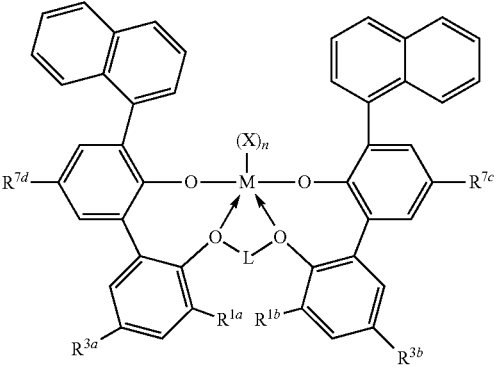

(Im)

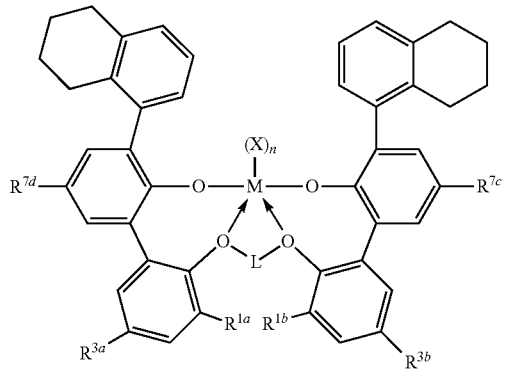

(In)

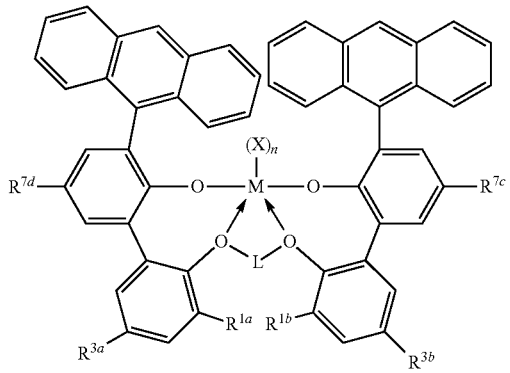

(Io)

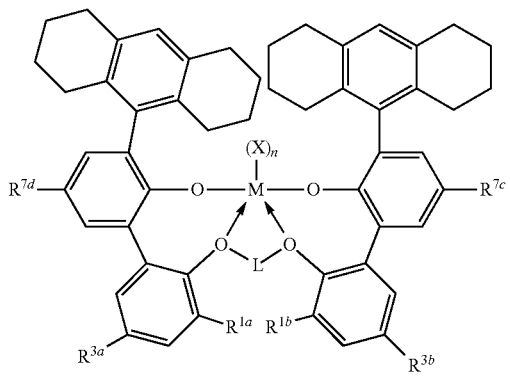

wherein M, X, $R^{1a}$, $R^{1b}$, $R^{3a}$, $R^{3b}$, $R^{7c}$, $R^{7d}$, and L are as defined previously and each $R^{55}$ and $R^{65}$ is as defined previously. Preferably each $R^{55}$ and $R^{65}$ independently is a hydrogen atom or an unsubstituted $(C_1-C_{12})$alkyl.

As mentioned above for the metal-ligand complex of any one of formulas (Ia) to (Io), the M, X, L, $R^{1a}$, $R^{2a}$, $R^{3a}$, $R^{1b}$, $R^{2b}$, $R^{3b}$, $R^{7c}$, and $R^{7d}$, as the case may be, are as defined for the same of formula (I) (i.e., as M, X, L, $R^{1a}$, $R^{2a}$, $R^{3a}$, $R^{1b}$, $R^{2b}$, $R^{3b}$, $R^{7c}$, and $R^{7d}$ of formula (I)). Preferably M is hafnium or zirconium. Preferably each X is a monodentate ligand. In some embodiments of the metal-ligand complex of any one of formulas (Ia) to (Io), n is 2 or 3 and at least two X independently are monoanionic monodentate ligands and a third X, if present, is a neutral monodentate ligand. In some embodiments L is —$CH_2CH_2$—, —$CH(CH_3)CH(CH_3)$—, —$CH_2C(CH_3)_2$—, or —$Si(CH_3)_2CH_2$—. In some embodiments each of $R^{1a}$, $R^{2a}$, $R^{3a}$, $R^{1b}$, $R^{2b}$, $R^{3b}$ independently is hydrogen atom, methyl; ethyl; 2-propyl; 1,1-dimethylethyl; mono-, di-, or trifluoromethyl; methoxy; ethoxy; 1-methylethoxy; mono-, di-, or trifluoromethoxy; halogen atom; cyano; nitro; dimethylamino; aziridin-1-yl; or cyclopropyl, wherein at least one of $R^{1a}$, $R^{2a}$, and $R^{3a}$ independently is not the hydrogen atom and at least one of $R^{1b}$, $R^{2b}$, and $R^{3b}$ independently is not the hydrogen atom. In some embodiments each of $R^{7c}$ and $R^{7d}$ independently is $(C_4-C_8)$alkyl.

The invention process employs catalytic amounts of the invention catalyst. When more than one catalyst is employed, each catalyst independently will be in a catalytic amount. The term "catalytic amount" means less than a stoichiometric quantity based on number of moles of a product-limiting stoichiometric reactant employed in the invention process. The catalytic amount is also equal to or greater than a minimum amount of the metal-ligand complex of formula (I) that is necessary for at least some product of the catalyzed reaction to be formed and detected (e.g., by mass spectrometry). The minimum catalytic amount preferably is 0.0001 mole percent of the number of moles of a product-limiting stoichiometric reactant. In the invention process the product-limiting stoichiometric reactant for the invention catalyst typically will be ethylene. Preferably, the catalytic amount of the metal-ligand complex of formula (I) used to prepare the invention catalyst is from 0.001 mol % to 50 mol % of the moles of ethylene or $(C_3-C_{40})\alpha$-olefin, whichever is lower. More preferably, the catalytic amount of the metal-ligand complex of formula (I) is at least 0.01 mol %, still more preferably at least 0.05 mol %, and even more preferably at least 0.1 mol %. Also more preferably, the catalytic amount of the metal-ligand complex of formula (I) is 40 mol % or less, and still more preferably 35 mol % or less.

Preferably the catalyst has a minimum catalyst efficiency or higher. The catalyst efficiency is calculated by dividing the number of grams of polyethylene, poly-α-olefin, or poly(co-ethylene-α-olefin), prepared by the number of grams of metal (M) in ingredient (a) (i.e., M in metal-ligand complex of formula (I)) employed (i.e., catalyst efficiency=g PE prepared/g M in metal-ligand complex of formula (I) employed). Preferably when the catalyst efficiency is determined employing ethylene and 1-octene at a polymerization reaction temperature of 170° C. and 0.10 micromole (μmol) of the metal-ligand complex of formula (I), 0.12 μmol of the activating co-catalyst, bis(octadecyl)methylammonium tetrakis(pentafluorophenyl)borate ([HNMe($C_{18}H_{37}$)$_2$][B($C_6F_5$)$_4$], abbreviated as BOMATPB), and 1.0 μmol of another activating co-catalyst that is a triisobutylaluminum-modified methylalumoxane-3A (MMAO-3A), hydrogen gas, and a mixed alkanes solvent, the catalyst efficiency is greater than 740,000, more preferably greater than 960,000, still more preferably greater than 1,480,000, and even more preferably greater than 1,900,000. Preferably when the catalyst efficiency is determined employing ethylene and 1-octene as described later at a polymerization reaction temperature of 170° C. and 0.08 μmol of the metal-ligand complex of formula (I), 0.096 μmol of the BOMATPB, and 0.8 μmol of MMAO-3A, the catalyst efficiency is greater than 1,1,480,000. Preferably when the catalyst efficiency is determined employing ethylene and 1-octene as described later at a polymerization reaction temperature of 170° C. and 0.075 μmol of the metal-ligand complex of formula (I), 0.09 μmol of the BOMATPB, and 0.75 μmol of MMAO-3A, the catalyst efficiency is greater than 970,000, more preferably greater than 1,060,000, and still more preferably greater than 1,090,000. Preferably when the catalyst efficiency is determined employing ethylene and 1-octene as described later at a polymerization reaction temperature of 170° C. and 0.05 μmol of the metal-ligand complex of formula (I), 0.06 μmol of the BOMATPB, and 0.5 μmol of MMAO-3A, the catalyst efficiency is greater than 920,000, more preferably greater than 940,000, and still more preferably greater than 2,900,000. More preferably the catalyst efficiency is as defined as in any one of the Examples described later.

In some embodiments, the catalyst, catalyst system or composition, or both further comprises one or more solvents, diluents, or a combination thereof. In other embodiments, the such may further comprise a dispersant, e.g., an elastomer, preferably dissolved in the diluent. In these embodiments, the catalyst is preferably homogeneous.

The invention further requires a cocatalyst for activation of the metal-ligand complex. Where there are two or more such cocatalysts, they can be activated by the same or different. Many cocatalysts and activating techniques have been previously taught with respect to different metal-ligand complexes in the following U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. Preferred cocatalysts (activating co-catalysts) for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is, for example, bulk electrolysis, which is well known to those skilled in the art. Combinations of one or more of the foregoing cocatalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Preferably the alkyl of the foregoing alkyl-aluminums is from 1 to 10 carbon atoms. Triethylaluminum is more preferred. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane. Other preferred cocatalysts are tri(($C_6$-$C_{18}$)aryl)boron compounds and halogenated (including perhalogenated) derivatives thereof, (e.g., tris(pentafluorophenyl)borane, trityl tetrafluoroborate, or, more preferably bis(octadecyl)methylammonium tetrakis (pentafluorophenyl)borane ([HNMe($C_{18}H_{37}$)$_2$]—[B($C_6F_5$)$_4$], abbreviated as BOMATPB)). In some embodiments at least two of the cocatalysts are used in combination with each other.

The ratio of total number of moles of one or more metal-ligand complexes of formula (I) to total number of moles of one or more of the activating co-catalysts is from 1:10,000 to 100:1. Preferably, the ratio is at least 1:5000, more preferably at least 1:1000; and 10:1 or less, more preferably 1:1 or less. When an alumoxane alone is used as the activating co-catalyst, preferably the number of moles of the alumoxane that are employed is at least 100 times the number of moles of the metal-ligand complex of formula (I). When tris(pentafluorophenyl)borane alone is used as the activating co-catalyst, preferably the number of moles of the tris(pentafluorophenyl)borane that are employed to the total number of moles of one or more metal-ligand complexes of formula (I) may vary from 0.5:1 to 10:1, more preferably from 1:1 to 6:1, and still more preferably from 1:1 to 5:1. The remaining activating co-catalysts are generally employed in mole quantities that are approximately equal to the total mole quantities of one or more metal-ligand complexes of formula (I).

In certain circumstances the comonomer incorporation index may be determined directly, for example, by the use of NMR spectroscopic techniques described previously or by IR spectroscopy. If NMR or IR spectroscopic techniques cannot be used, then any difference in comonomer incorporation is indirectly determined. For polymers formed from multiple monomers this indirect determination may be accomplished by various techniques based on monomer reactivities.

Olefin polymerizing conditions employed herein independently refer to reaction conditions such as solvent(s), atmosphere(s), temperature(s), pressure(s), time(s), and the like that are preferred for producing, after 15 minutes reaction time, at least a 10 percent (%), more preferably at least 20%, and still more preferably at least 30% reaction yield of the polyethylene, poly-α-olefin, or poly(co-ethylene-α-olefin) having a molecular weight less than 2500 Da from the invention process. Preferably, the process is independently run under an inert atmosphere (e.g., under an inert gas consisting essentially of, for example, nitrogen gas, argon gas, helium gas, or a mixture of any two or more thereof). Other atmospheres are contemplated, however, and these include sacrificial olefin in the form of a gas and hydrogen gas (e.g., as a polymerization termination agent). In some aspects, the process may be run neat, without solvent and with or without additional ingredients (e.g., catalyst stabilizer such as triphenylphosphine). In still other aspects, it may be run with a solvent or mixture of two or more solvents, e.g., an aprotic solvent. Preferably, the neat process or solvent-based process is run at a temperature of the neat mixture or solvent-containing mixture of at least 30° C. to 300° C. A convenient temperature is from about 40° C. to about 300° C., and various embodiments may be run in a range from 60° C., or 100° C., or 120° C., to 250° C., or 230° C., or 190° C., or 170° C. Preferably the process is run under a pressure from about 0.9 atmospheres (atm) to about 50 atm (i.e., from about 91 kiloPascals (kPa) to about 5050 kPa).

In some embodiments, polymerizable olefins useful in the invention process are ($C_2$-$C_{40}$)hydrocarbons consisting of carbon and hydrogen atoms and containing at least 1, and preferably no more than 3, and more preferably no more than 2, carbon-carbon double bonds. In some embodiments, from 1 to 4 hydrogen atoms of the ($C_2$-$C_{40}$)hydrocarbons are replaced, each by a halogen atom, preferably fluoro or chloro to give halogen atom-substituted ($C_2$-$C_{40}$)hydrocarbons as the useful polymerizable olefins. The ($C_2$-$C_{40}$) hydrocarbons (not halogen atom-substituted) are preferred. Preferred polymerizable olefins (i.e., olefin monomers) useful for making the polyolefins are ethylene and polymerizable ($C_3$-$C_{40}$)olefins. The ($C_3$-$C_{40}$)olefins include an α-olefin, a cyclic olefin, styrene, and a cyclic or acyclic diene. In some embodiments at least one of the other polymerizable olefin is the α-olefin, and more preferably a ($C_3$-$C_{40}$)α-olefin. In some embodiments the ($C_3$-$C_{40}$) α-olefin is a ($C_4$-$C_{40}$)α-olefin, more preferably a ($C_6$-$C_{40}$) α-olefin, still more preferably a ($C_7$-$C_{40}$)α-olefin, and even more preferably a ($C_8$-$C_{40}$)α-olefin. Preferably, the α-olefin comprises the ($C_3$-$C_{40}$)α-olefin, more preferably a branched chain ($C_3$-$C_{40}$)α-olefin, still more preferably a linear-chain ($C_3$-$C_{40}$)α-olefin, even more preferably a linear chain ($C_3$-$C_{40}$)α-olefin of formula (A): $CH_2=CH_2-(CH_2)_zCH_3$ (A), wherein z is an integer of from 0 to 40, and yet even more preferably a linear-chain ($C_3$-$C_{40}$)α-olefin that is 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, or a linear-chain ($C_{20}$-$C_{24}$)α-olefin. Preferably the cyclic olefin is a (C$_3$-C$_{40}$)cyclic olefin. Preferably, the cyclic or acyclic diene is a (C$_4$-C$_{40}$)diene, preferably an acyclic diene, more preferably an acyclic conjugated (C$_4$-C$_{40}$)diene, more preferably an acyclic 1,3-conjugated (C$_4$-C$_{40}$)diene, and still more preferably 1,3-butadiene.

Polyolefins that can be made by an invention process include, for example, polyethylene and interpolymers that comprise residuals of ethylene and one or more polymerizable (C$_3$-C$_{40}$)olefins. Preferred interpolymers are those prepared by co-polymerizing a mixture of two or more polymerizable olefins such as, for example, ethylene/propylene, ethylene/1-butene, ethylene/1-pentene, ethylene/1-hexene, ethylene/4-methyl-1-pentene, ethylene/1-octene, ethylene/styrene, ethylene/propylene/-butadiene and other EPDM terpolymers. Preferably, the polyolefin is an ethylene homopolymer (e.g., a high density polyethylene), an ethylene/α-olefin interpolymer (i.e., poly(co-ethylene α-olefin), such as, for example, a poly(ethylene 1-octene)), or an ethylene/α-olefin/diene interpolymer (i.e., a poly(ethylene α-olefin diene)terpolymer such as, for example, a poly(ethylene 1-octene 1,3-butadiene).

Preferably, the mole ratio of (moles of (C$_3$-C$_{40}$)α-olefin)/(moles of ethylene) is 0.1 or higher, more preferably 0.30 or higher, still more preferably 0.50 or higher, and even more preferably 0.75 or higher (e.g., 1.0 or higher).

In another embodiment, the present invention is a polyolefin, preferably the polyethylene (e.g., in an isolated form or as part of an intermediate mixture with the α-olefin) prepared by the invention process.

The inventive process may be run in one reactor or in multiple reactors. For example, single reactor, multiple catalyst processes are useful in the present invention. In one embodiment, two or more catalysts are introduced into a single reactor under the olefin polymerization conditions, wherein at least the first one of the catalysts is a catalyst of the group specified herein and each catalyst inherently produces a mixture or blend of different polyolefin copolymers. The terms "mixture" and "blend" as applied to the polyolefin copolymers are synonymous. Use of different catalysts within the invention may result in similar or different comonomer incorporation, but products within the invention will fall into a weight average molecular weight range of less than 2500 Da, preferably less than 1500 Da. Variation of the ratio of two or more catalysts within a single reactor will vary the product ratio, and knowledge of such is within that of those skilled in the art. See also, U.S. Pat. No. 6,924,342. The invention catalysts are compatible with other olefin polymerization catalysts, including Ziegler/Natta catalysts. Due to this compatibility, an additional catalyst included in one reaction may comprise a metallocene or other π-bonded ligand group containing metal-ligand complex (including constrained geometry metal-ligand complexes), or a polyvalent heteroatom ligand group containing metal-ligand complex, especially polyvalent pyridylamine or imidizolylamine based complexes and tetradentate oxygen-ligated biphenylphenol based Group 4 metal-ligand complexes. Preferably, the invention catalyst is prepared from, and the invention process employs, three or fewer, more preferably two, and still more preferably one metal-ligand complex of formula (I) per reactor. Further discussion of such may be found in co-pending U.S. Patent Publication No. 2011/0282018, filed May 11, 2011.

In some embodiments a preferred invention process can achieve a minimum molecular weight distribution or polydispersity index (PDI) of the polyolefin product produced thereby. In some embodiments the PDI is greater than 2.4, in other embodiments the PDI is greater than 4.0, in other embodiments the PDI is greater than 6.0, and in still other embodiments the PDI is greater than 8.0. In some embodiments the PDI is less than 11.

In some embodiments a preferred invention process can achieve a productivity ratio of weight of polyolefin produced per weight of ethylene employed, as determined employing ethylene and 1-octene as described later at a polymerization reaction temperature of 170° C., wherein the productivity ratio of the polyolefin produced to ethylene employed is greater than 1.00, preferably greater than 1.10, more preferably greater than 1.40, and still more preferably greater than 2.50.

EXAMPLES

General Analysis Procedures

Gel permeation chromatography (GPC): Determine weight average molecular weight (M$_w$) and polydispersity index: Determine M$_w$ and ratio of M$_w$/M$_n$ (polydispersity index or PDI) using a Polymer Labs™ 210 high temperature gel permeation chromatograph. Prepare samples using 13 mg of polyethylene polymer that is diluted with 16 mL of 1,2,4-trichlorobenzene (stabilized with butylated hydroxy toluene (BHT)), heat and shake at 160° C. for 2 hours.

Determining melting and crystallization temperatures and heat of fusion by Differential Scanning Calorimetry (DSC; DSC 2910, TA Instruments, Inc.)); First heat samples from room temperature to 180° C. at a heating rate of 10° C. per minute. After being held at this temperature for 2 to 4 minutes, cool the samples to −40° C. at a cooling rate of 10° C. per minute; hold the sample at the cold temperature for 2 to 4 minutes, and then heat the sample to 160° C.

Abbreviations (meanings): r.t. (room temperature); g (gram(s)); mL (milliliter(s)); ° C. (degrees Celsius); mmol (millimole(s)); MHz (MegaHertz); Hz (Hertz).

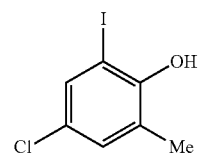

Starting Compound

Synthesis Procedures for Metal-Ligand Complexes

Step 1: Preparation of 4-chloro-2-iodo-6-methylphenol

To a stirred solution of 5.08 g (35.63 mmol) of 4-chloro-2-methylphenol, 6.42 g (42.83 mmol) of NaI, and 1.74 g (43.50 mmol) of NaOH in 70 mL of methanol at 0-10° C. is added 71 mL (47.69 mmol) of 5% aqueous NaOCl solution (commercial bleach) dropwise over 1.5 hours. After addition of NaOCl solution is complete the reaction mixture is stirred for an additional hour at 0-10° C., then 25 mL of 10 wt. % aqueous sodium thiosulfate is added. The mixture is acidified using 5% HCl, then extracted with methylene chloride (i.e., dichloromethane, DCM). The combined organic phases are washed with an equal volume each of 10 wt. % aqueous sodium thiosulfate, then water, then brine, then dried over anhydrous magnesium sulfate, then filtered through a pad of silica gel, and then concentrated to give crude compound. This crude is recrystallized from hexanes to afford 9.37 g (98%) product as white needles. $^1$H NMR showed product is 4-chloro-2-iodo-6-methylphenol.

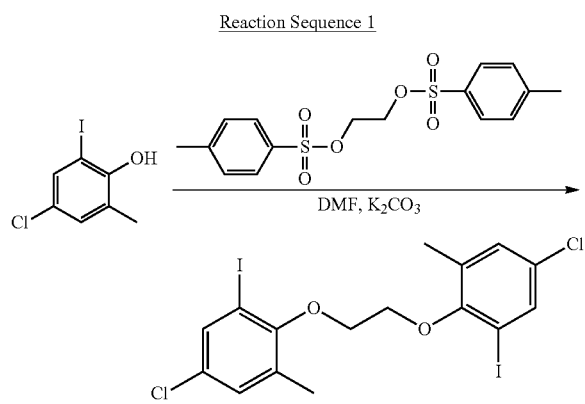

Reaction Sequence 1

Step 2: Preparation of 1,2-bis(4-chloro-2-iodo-6-methylphenoxy)ethane

To a round bottom flask under $N_2$ atmosphere is added 6.00 g (22.35 mmol) of 4-chloro-2-iodo-6-methylphenol, 6.18 g (44.72 mmol) of $K_2CO_3$, 45 mL of DMF, and 4.14 g (11.18 mmol) of ethylene glycol ditosylate. The mixture is stirred and refluxed for 18 hours, cooled and concentrated. The residue is treated with 50/50 DCM and water until all solids are dissolved and then transferred the mixture to a separation funnel where the compound is extracted into DCM. The organic solution is washed with 2N NaOH, water then brine, dried over anhydrous magnesium sulfate, filtered through a pad of silica gel and concentrated to give 4.56 g (72.5%) of pure product as white solid. $^1$H NMR shows product is 1,2-bis(4-chloro-2-iodo-6-methylphenoxy)ethane.

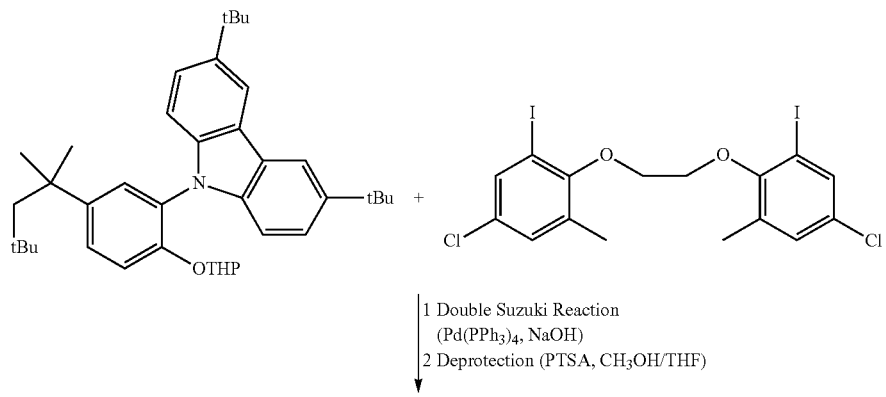

Reaction Sequence 2

1 Double Suzuki Reaction (Pd(PPh$_3$)$_4$, NaOH)
2 Deprotection (PTSA, CH$_3$OH/THF)

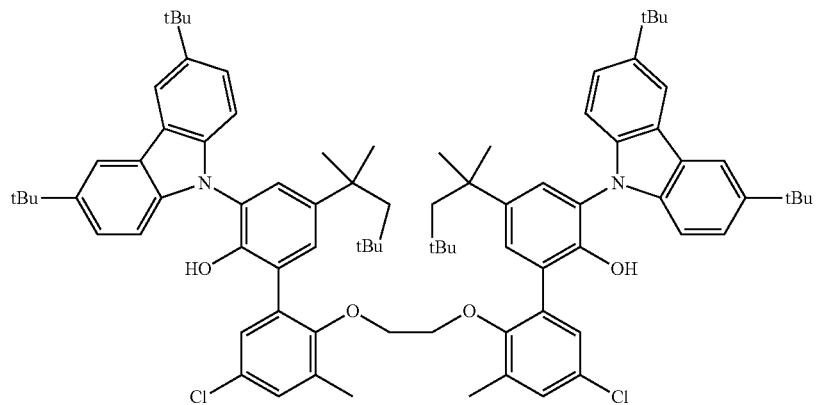

Step 3: Preparation of 2',2'''-(ethane-1,2-diylbis (oxy))bis(3-(3,6-di-tert-butyl-9H-carbazol-9-yl)-5'-chloro-3'-methyl-5-(2,4,4-trimethylpentan-2-yl)-[1,1'-biphenyl]-2-ol)

To a stirred solution of 5.0 g (8.82 mmol) of 3,6-di-tert-butyl-9-(2-(methoxymethoxy)-5-(2,4,4-trimethylpentan-2-yl)phenyl)-9H-carbazole in 75 mL of tetrahydro-furan (THF) at 0° C. under nitrogen atmosphere 8.1 mL (20.25 mmol) of n-butyllithium (2.5 M solution in hexanes) is added over a period of 10 minutes. The solution is stirred at 0° C. for three more hours. Tri-isopropyl borate (4.8 mL, 20.8 mmol) is added to this and continued stirring at 0° C. for 1 hour. The mixture is slowly warmed to room temperature and stirred for 3 more hours at room temperature. The mixture is concentrated to dryness by rotary evaporation and 100 mL of ice cold water is added. The mixture is acidified using 2N HCl and extracted with dichloromethane (DCM). The DCM solution is washed with water and brine. The solvent is removed by rotary evaporation and the residue is dissolved in 90 mL of dimethoxyethane. This solution is then treated with a solution of 1.06 g (26.5 mmol) of NaOH in 25 mL of water, 25 mL of THF and 2.35 g (4.17 mmol) of 1,2-bis(4-chloro-2-iodo-6-methylphenoxy)ethane. The system is purged with N and 0.30 g (0.26 mmol) of Pd(PPh$_3$)$_4$ is added. The mixture is then heated to 85° C. for 36 hours under N atmosphere. The mixture is cooled and the volatiles removed by rotary evaporation. The residue is treated with 100 mL of water and extracted with DCM. The DCM solution is washed with water and brine, and dried over anhydrous magnesium sulfate. After removal of the solvent, the reaction products are dissolved in 150 mL of THF/MeOH (1:1) and stirred for 5 hours at 50° C. after the addition of 100 mg of p-toluenesulfonic acid. The solvent is removed and the product is partially purified by flash chromatography eluting with 5% ethyl acetate in hexanes. This product is further purified by crystallization from THF/MeOH (dissolved in minimum amount of THF and diluted with MeOH until it became cloudy. It is then heated to obtain a clear solution and allowed to crystallize in refrigerator). The solid formed is collected and dried under reduced pressure to afford 3.5 g (62.5%) of the pure ligand as white solid. $^1$H NMR shows the product is 2',2'''-(ethane-1,2-diylbis(oxy))bis(3-(3,6-di-tert-butyl-9H-carbazol-9-yl)-5'-chloro-3'-methyl-5-(2,4,4-trimethylpentan-2-yl)-[1,1'-biphenyl]-2-ol).

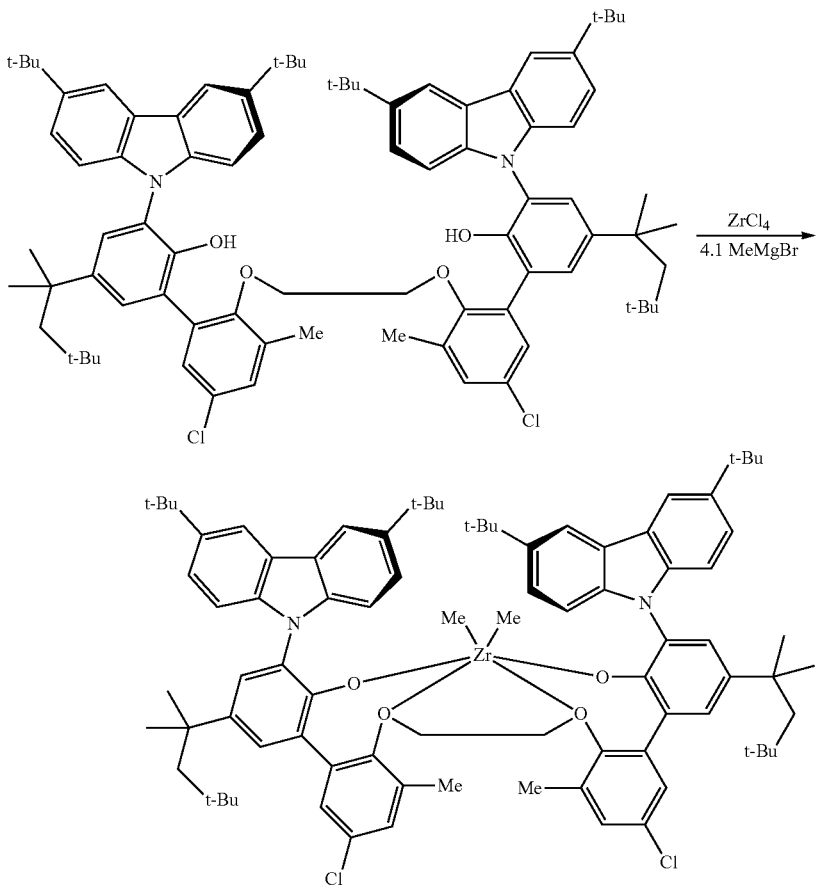

Reaction Sequence 3

Step 4: Preparation of (2',2'''-(ethane-1,2-diylbis (oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-zirconium (Metal-Ligand Complex 1)

To a suspension of 0.75 g (0.59 mmol) of 2',2'''-(ethane-1,2-diylbis(oxy))bis(3-(3,6-di-tert-butyl-9H-carbazol-9-yl)-5'-chloro-3'-methyl-5-(2,4,4-tri-methylpentan-2-yl)-[1,1'-biphenyl]-2-ol) and 0.137 g (0.59 g) of HfCl$_4$ in 50 mL of toluene is added 0.84 mL of 3M diethyl ether solution of MeMgBr. After stirring for 1 hr solvent is removed under reduced pressure. To the residue is added 20 mL of toluene followed by 30 mL of hexane. Suspension is filtered giving colorless solution. Solvent is removed under reduced pressure leaving white solid. The residue is suspended in 15 mL of hexane and suspension is stirred for 30 min. The solid is collected on the frit, washed with 3 mL of hexane and dried under reduced pressure to give 0.545 g of product as white solid. $^1$H NMR shows the product is (2',2''-(ethane-1,2-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-zirconium (Metal-Ligand Complex 1).

Reaction Sequence 4

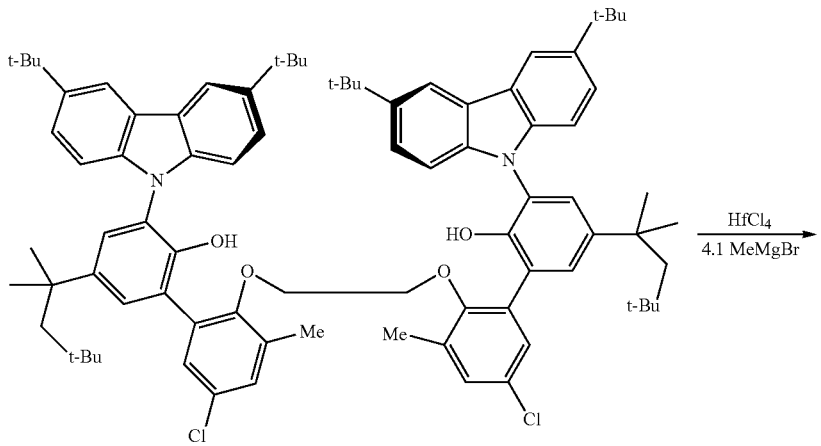

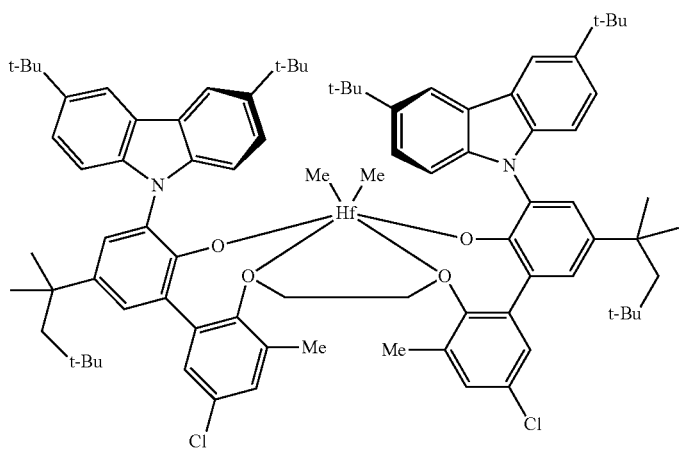

Alternative Step 4: Preparation of 2',2''-(ethane-1,2-diylbis(oxy))bis(5'-chloro-3-(3,6-di-tert-butyl-9H-carbazol-9-yl)-3'-methyl-5-(2,4,4-trimethylpentan-2-yl)biphenyl-2-ol)dimethyl-hafnium (Metal-Ligand Complex 2)

To a suspension of 1.94 g (1.52 mmol) of ligand and 0.488 g (1.52 mmol) HfCl$_4$ in 50 mL of toluene is added 2.18 mL of 3M diethyl ether solution of MeMgBr. After stirring for 1 hr solvent is removed under reduced pressure. To the residue is added 30 mL of toluene followed by 30 mL of hexane. Suspension is filtered giving colorless solution. Solvent is removed under reduced pressure leaving white solid. The residue is suspended in 12 mL of hexane and suspension is stirred for 30 min. The solid is collected on the frit, washed with 3 mL of hexane and dried under reduced pressure to give 1.81 g of product as white solid. Yield is 80.3%. $^1$H NMR spectra of this product are consistent with the desired structure.

A comparative complex is also prepared and designated as (Metal-Ligand Complex 3—comparative), as shown hereinbelow.

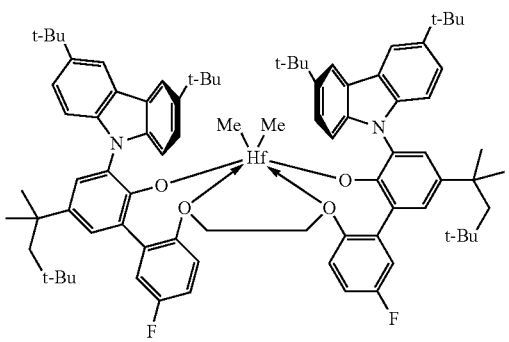

(Metal-Ligand Complex 3—comparative)

Examples 1-2 and Comparative Example A

Ethylene is polymerized independently using the Metal-Ligand Complexes (1) and (2), corresponding to Examples 1 and 2, and the comparative Metal-Ligand Complex (3), corresponding to Comparative Example A, under the following conditions: 2 L batch reactor, 140° C., 783 g of isoparE, a saturated isoparaffinic hydrocarbon fluid available from ExxonMobil. Conditions include ethylene pressure of 460 psi; run time of 10 min. Results include catalyst efficiency (gPE/gM), calculated by dividing weight in grams of PE product by weight in grams of metal M in metal-ligand complex used. $M_w$ (g/mol) is weight average molecular weight in grams per mole determined by GPC; $M_w/M_n$=polydispersity index (PDI)=$M_w$ divided by number average molecular weight ($M_n$) (g/mol). Results are shown in Table 1.

TABLE 1

| Polymerization of Ethylene | | | | | | |
|---|---|---|---|---|---|---|
| Metal-Ligand Complex | | | | Efficiency/ | | |
| Name | moles | metal | (g) | g Metal | Mw | Mw/Mn |
| 1 | 0.03 | Zr | 8.3 | 3032828 | 338 | 1.19 |
| 2 | 0.04 | Hf | 13.2 | 1848843 | 599 | 1.47 |
| Comp. Ex. A | 0.05 | Hf | 4.7 | 526640 | 2,703 | 2.06 |

As shown by the above description, including the Examples, the invention catalysts prepared from the invention metal-ligand complexes polymerize ethylene, α-olefin or ethylene with α-olefin to yield the low molecular weight polyethylene, poly-α-olefin or poly(co-ethylene-α-olefin) having a backbone weight average molecular weight of less than 2500 Da. The invention process is also useful for preparing the aforementioned polymer blends with good catalyst efficiency.

What is claimed is:
1. A process for preparing a low molecular weight ethylene-based material comprising a step of contacting together (1) a monomer selected from (a) ethylene; (b) a non-ethylene α-olefin; or (c) a combination thereof; and (2) a catalytic amount of a catalyst; wherein the catalyst comprises a mixture or reaction product of ingredients (2a) and (2b) that is prepared before the contacting step, wherein ingredient (2a) is at least one metal-ligand complex, and wherein ingredient (2b) is at least one activating co-catalyst; the metal-ligand complex of ingredient (2a) being at least one metal-ligand complex of formula (I):

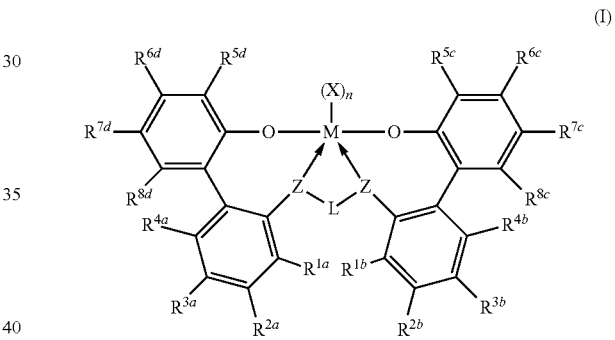

wherein M is titanium, zirconium, or hafnium, each independently being in a formal oxidation state of +2, +3, or +4; n is an integer from 0 to 3, wherein when n is 0, X is absent; each X independently is a monodentate ligand that is neutral, monoanionic, or dianionic, or two X are taken together to form a bidentate ligand that is neutral, monoanionic, or dianionic; X and n are chosen in such a way that the metal-ligand complex of formula (I) is, overall, neutral; each Z independently is O, S, N($C_1$-$C_{40}$)hydrocarbyl, or P($C_1$-$C_{40}$)hydrocarbyl; L is ($C_1$-$C_{40}$)hydrocarbylene or ($C_1$-$C_{40}$) heterohydrocarbylene, wherein the ($C_1$-$C_{40}$)hydrocarbylene has a portion that comprises a 2-carbon atom linker backbone linking the Z atoms in formula (I) and the ($C_1$-$C_{40}$) heterohydrocarbylene has a portion that comprises a 2-atom atom linker backbone linking the Z atoms in formula (I), wherein each atom of the 2-atom linker of the ($C_1$-$C_{40}$) heterohydrocarbylene independently is a carbon atom or a heteroatom, wherein each heteroatom independently is O, S, S(O), S(O)$_2$, Si($R^C$)$_2$, Ge($R^C$)$_2$, P($R^P$), or N($R^N$), wherein independently each $R^C$ is unsubstituted ($C_1$-$C_{18}$)hydrocarbyl or the two $R^C$ are taken together to form a ($C_2$-$C_{19}$)alkylene, each $R^P$ is unsubstituted $(C_1-C_{18})$hydrocarbyl; and each $R^N$ is unsubstituted $(C_1-C_{18})$hydrocarbyl, a hydrogen atom or absent; at least one of $R^{1a}$, $R^{2a}$, $R^{1b}$, and $R^{2b}$ independently is a $(C_1-C_{40})$hydrocarbyl, $(C_1-C_{40})$heterohydrocarbyl, $N(R^N)_2$, $NO_2$, $OR^C$, $SR^C$, $Si(R^C)_3$, $Ge(R^C)_3$, CN, $CF_3$, $F_3CO$, halogen atom; and each of the others of $R^{1a}$, $R^{2a}$, $R^{1b}$, and $R^{2b}$ independently is a hydrogen, $(C_1-C_{40})$hydrocarbyl, $(C_1-C_{40})$heterohydrocarbyl, $N(R^N)_2$, $NO_2$, $OR^C$, $SR^C$, $Si(R^C)_3$, CN, $CF_3$, $F_3CO$ or halogen atom; each of $R^{3a}$, $R^{4a}$, $R^{3b}$, $R^{4b}$, $R^{6c}$, $R^{7c}$, $R^{8c}$, $R^{6d}$, $R^{7d}$, and $R^{8d}$ independently is a hydrogen atom; $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)$—, $R^CS(O)_2$—, $(R^C)_2C=N$—, $R^CC(O)O$—, $R^COC(O)$—, $R^CC(O)N(R)$—, $(R^C)_2NC(O)$— or halogen atom; each of $R^{5c}$ and $R^{5d}$ independently is a $(C_6-C_{40})$aryl or $(C_1-C_{40})$heteroaryl; each of the aforementioned aryl, heteroaryl, hydrocarbyl, heterohydrocarbyl, hydrocarbylene, and heterohydrocarbylene groups independently is unsubstituted or substituted with one or more substituents $R^S$; and each $R^S$ independently is a halogen atom, polyfluoro substitution, perfluoro substitution, unsubstituted $(C_1-C_{18})$alkyl, $F_3C$—, $FCH_2O$—, $F_2HCO$—, $F_3CO$—, $R_3Si$—, $R_3Ge$—, RO—, RS—, RS(O)—, $RS(O)_2$—, $R_2P$—, $R_2N$—, $R_2C=N$—, NC—, RC(O)O—, ROC(O)—, RC(O)N(R)—, or $R_2NC(O)$—, or two of the $R^S$ are taken together to form an unsubstituted $(C_1-C_{18})$alkylene, wherein each R independently is an unsubstituted $(C_1-C_{18})$alkyl; such that the ratio of total number of moles of the at least one metal-ligand complex (2a) to total number of moles of the at least one activating co-catalyst (2b) is from 1:10,000 to 100:1; under conditions such that a polyethylene, poly-α-olefin, or poly(co-ethylene-α-olefin), having a backbone weight average molecular weight (Mw) that is less than 1500 daltons (Da), is formed.

2. The process of claim 1 wherein M is zirconium or hafnium.

3. The process of claim 1 wherein each Z is O.

4. The process of claim 1 wherein $R^{1a}$ and $R^{1b}$ are methyl, ethyl or isopropyl.

5. The process of claim 1 wherein $R^{1a}$ and $R^{1b}$ are fluorine atoms, chlorine atoms, bromine atoms or iodine atoms.

6. The process of claim 1 wherein L is —$CH_2CH_2$—, —$CH(CH_3)CH(CH_3)$—, 1,2-cyclopentanediyl or 1,2-cyclohexane-diyl.

7. The process of claim 1 wherein $R^{5d}$ independently is a 2,7-disubstituted 9H-carbazol-9-yl or a 3,6-disubstituted 9H-carbazol-9-yl, 9H-carbazol-9-yl, wherein each substituent is $R^S$.

8. The process of claim 1 wherein $R^{5d}$ independently is a $(C_6-C_{40})$aryl that is a 2,4-disubstituted phenyl, wherein each substituent is $R^S$; 2,5-disubstituted phenyl wherein each substituent is $R^S$; 2,6-disubstituted phenyl wherein each substituent is $R^S$; 3,5-disubstituted phenyl wherein each substituent is $R^S$; 2,4,6-trisubstituted phenyl wherein each substituent is $R^S$; naphthyl or substituted naphthyl wherein each substituent is $R^S$; 1,2,3,4-tetrahydronaphthyl; anthracenyl; 1,2,3,4-tetrahydroanthracenyl; 1,2,3,4,5,6,7,8-octahydroanthracenyl; phenanthrenyl; or 1,2,3,4,5,6,7,8-octahydrophenanthrenyl.

9. The process of claim 1 wherein the conditions include a temperature from 30° C. to 300° C.

\* \* \* \* \*